(12) United States Patent
London et al.

(10) Patent No.: US 6,706,528 B2
(45) Date of Patent: Mar. 16, 2004

(54) FLUORESCENT MAGNESIUM INDICATORS

(75) Inventors: Robert E. London, Chapel Hill, NC (US); Pieter Otten, Escondido, CA (US); Louis A. Levy, Chapel Hill, NC (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/816,638

(22) Filed: Mar. 23, 2001

(65) Prior Publication Data

US 2002/0031834 A1 Mar. 14, 2002

Related U.S. Application Data

(60) Provisional application No. 60/191,862, filed on Mar. 24, 2000.

(51) Int. Cl.[7] ............................................. G01N 21/64
(52) U.S. Cl. .......................................... 436/79; 436/172
(58) Field of Search .................................. 436/172, 79

(56) References Cited

U.S. PATENT DOCUMENTS

| | | | | |
|---|---|---|---|---|
| 4,001,243 A | * | 1/1977 | Gerster | 544/126 |
| 4,339,582 A | * | 7/1982 | Van Dyke, Jr. | 514/872 |
| 4,698,349 A | * | 10/1987 | Kitaura et al. | 514/306 |
| 6,235,751 B1 | * | 5/2001 | Park et al. | 514/306 |

FOREIGN PATENT DOCUMENTS

JP          63-225375        *  9/1988

OTHER PUBLICATIONS

Acheson, D.M. et al, Chemical Abstracts, vol. 62, No. 13, abstract No. 16188h, Jun. 21, 1965.*

Fujisawa Pharmaceutical Co., Chemical Abstracts, vol. 110, No. 25, abstract No. 231452e, Jun. 19, 1989.*

* cited by examiner

*Primary Examiner*—Jeffrey Snay
(74) *Attorney, Agent, or Firm*—Jeffrey I. Auerbach; Liniak, Berenato & White

(57) ABSTRACT

The present invention generally relates to analytical elements and methods for the selective determination of magnesium. In particular, the present invention is further directed to carboxy-quinolizine suitable for use as magnesium indicators, and more particularly, to 4-oxo-4H-quinolizine-3-carboxylic acid derivatives for use as novel fluorescent magnesium indicators.

14 Claims, 20 Drawing Sheets

A.

B.

FLUORESCENT MAGNESIUM INDICATORS

The present application claims benefit of U.S. Provisional Patent Application Ser. No. 60/191,862, filed on Mar. 24, 2000.

FIELD OF THE INVENTION

The present invention generally relates to analytical elements and methods for the selective determination of magnesium. In particular, the present invention relates to carboxy-quinolizines and their use as magnesium indicators.

BACKGROUND OF THE INVENTION

Magnesium is the most abundant intracellular ion in the body next to potassium, and plays a central role in the biochemistry of all cells. Over three hundred magnesium-dependent enzymes have been identified (See e.g., Elin et al., Am. J. Clin. Pathol. 102: 616–622 [1994]). Magnesium is essential to many physicochemical processes including the activation of ATP in the transfer of energy rich phosphate. This magnesium-dependent ATP phosphorylation is central to cellular energetics and signaling (See, Elin et al., supra; Vescovi et al., Cell 84: 165–174 [1996]; Chelen et al., J. Biol. Chem. 274: 7059–7066 [1999]; Pan et al., J. Biol. Chem. 271: 1322–1328 [1996]; and Agus et al., Ann. Rev. Physiol. 53: 299–307 [1991]). In addition, magnesium plays a vital role in the activation of enzymes involved in lipid, carbohydrate, and protein metabolism, and the preservation of the macromolecular structure of DNA, RNA and ribosomes. Magnesium also has a significant influence on the neuromuscular apparatus. Decreased concentrations of magnesium may result in tetany and convulsions, while increased levels can cause general anesthesia, respiratory failure and cardiac arrest. Because tetany due to reduced magnesium concentrations is clinically indistinguishable from that caused by low calcium levels, it is frequently necessary to perform assays for both serum magnesium and calcium at the same time.

In addition, many epidemiological studies suggest links between plasma free magnesium levels and various diseases. Suggestive correlations have been reported linking magnesium levels to ischaemic heart disease, hypertension, atherosclerosis, osteoporosis, migraines, and many other chronic illnesses (See, Ford et al., Int. J. Epidemiol. 28: 645–651 [1999]; Altura et al., Cell Mol. Biol. Res. 41: 347–359 [1995]; Orimo et al., Ann. NY Acad. Sci. 598: 444–457 [1990]; Sojka et al., Nutrition Rev. 53: 71–74 [1995]; and Ramadan et al., Headache 29: 590–593 [1989]). In general, those correlations have been modest and the results often difficult to reproduce. A major reason for this limitation may be the difficulty of accurately assessing magnesium levels, and particularly the intracellular ionized magnesium concentration.

Because of the important role that magnesium plays in the normal functioning of life processes, it has long been recognized that it is necessary to be able to accurately and reliably measure magnesium levels in the body. Such measurements are particularly useful for the diagnoses and treatment of diseases. Many methods have been used to determine magnesium levels in biological fluids, including precipitation techniques, complexometric titration procedures, dye absorption methods, techniques utilizing cation-selective electrodes, absorption spectrometry, and fluorescent spectrophotometry.

One precipitation method for determining magnesium involves the precipitation of magnesium as magnesium ammonium phosphate. The phosphorus in the precipitate is then quantified by a variety of means, among which are photometric measurement as molybdenum blue or as the molybdivanadate complex. Following determination of the phosphate content, magnesium concentration is calculated mathematically. This method requires the elimination of phosphate contamination of the precipitate and the removal of interfering calcium ion, which results in inaccurate magnesium determinations. Thus, this method is cumbersome, time-consuming, and often lacks accuracy. Another precipitation method involves the precipitation of magnesium with 8-hydroxyquinoline. The precipitate can then be quantitated by titrimetry, colorimetry, flame photometry or fluorometry. As with phosphate precipitation techniques, calcium interference must be eliminated, and these procedures suffer the same drawbacks of being tedious, time-consuming, and lacking in accuracy. In addition, this precipitation technique requires special instrumentation that may not be easily available to smaller laboratories.

Various titrimetric techniques are used for the determination of magnesium based on titrations with the complexing agent EDTA (ethylenediamine-tetraacetic acid) using a variety of indicators such as Eriochrome Black T (3-hydroxy-4-[(1-hydroxy-2-naphthalenyl)azo]-7-nitro-1-naphthalene-sulfonic acid monosodium salt). Since calcium is also chelated by EDTA, calcium concentration must be established, either by a second titration or other means, and the magnesium level then calculated as the difference. However, it is often difficult to produce measurements with much precision or accuracy due to the largely subjective measurements of the color change at the titration endpoint, which may vary according to the rate of titration, or may be gradual in the presence of protein or moderately high levels of phosphate (e.g., as in urine and serum samples derived from patients suffering from renal failure).

Another method for determining magnesium involves dye absorption methods utilizing Titan Yellow. However, the colloidal or unevenly dispersed nature of the magnesium hydroxide-dye cake generally affects the accuracy of this method, resulting in erratic measurements which do not agree with those obtained by atomic absorption. In addition, this method suffers from other drawbacks, including the need for preparing a protein-free filtrate, limited sensitivity, color instability, and significant interference from calcium gluconate which is frequently administered in clinical situations where magnesium levels are being monitored.

Direct calorimetric dye-complexing methods using the indicators Magon, methylthymol blue, and Calmagite have recently become increasingly popular. The use of Magon was first reported by Mann et al., (Mann et al., Anal. Chem. 28: 202–205 [1956]) and by Bohoun (Bohoun, Coin. Chim. Acta 7: 811–817 [1962]). Currently used modifications of these original methods are relatively fast and simple to perform. However, these methods generally suffer from significant interference, and have been shown to produce erroneous results in the presence of citrate, a common constituent of intravenous fluids and blood used for transfusions. In addition, the reagents used in the determination of magnesium by reaction with Calmagite are somewhat unstable.

Atomic absorption is perhaps the most accurate means of determining magnesium levels. When light from a lamp containing a magnesium electrode passes through a flame which contains vapors of a fluid whose magnesium content is to be measured, the amount of light that is absorbed by the flame is directly proportional to the magnesium concentration. The intensity of the emerging light beam passes via a monochromator to a photomultiplier detector. Although this method is generally considered to be the reference method for magnesium determinations, expensive instrumentation required for atomic absorption spectroscopy limits its routine use in the clinical laboratory.

Magnesium ion selective electrodes have recently been used as magnesium indicators (Elin et al., Scand. J. Clin. Lab. Invest. Suppl. 224: 203–210 [1996]; Cecco et al., Am. J. Clin. Pathol. 108: 564–569 [1997[; Huijgen et al., Clin. Chem. Lab. Med. 37: 465–470 [1999]; Hristova et al., Clin. Chem. 43: 394–399 [1997]; and Rehak et al., Clin. Chem. 43: 1395–15600 [1997]). However, ionized magnesium concentrations determined using magnesium selective electrodes have been reported to vary with the concentration of calcium, and with the electrode manufacturer. In studies of serum derived from chronic alcoholics, results for ionized magnesium were found to be instrument dependent, so that the usefulness of the measurement could not be evaluated. Thus, it appears that magnesium selective electrodes for measuring ionized magnesium in serum and plasma give irreproducible results (Hristova et al., supra; Rehak et al., supra; and Csako et al., Eur. J. Clin. Chem. Clin. Biochem. 35: 701–709 [1997]). In addition, thiocyanate present in serum derived from smokers has been reported to interfere with free magnesium determination using ion selective electrodes. In patients with severe hypomagnesemia, values for ionized magnesium determined using ion selective electrodes were found to exceed values for total magnesium in some cases.

Fluorescence spectroscopy is a useful tool in monitoring intracellular levels of magnesium. This methodology is considered non-invasive since only a minute amount of the fluorescent metal chelator is loaded in the cell. The response time of fluorescence lies in the millisecond domain. Thus, ion fluxes induced by an extra-cellular stimulus can be monitored immediately. A commonly used fluorescent indicator is 8-hydroxyquinoline. However, the accuracy of observed results using 8-hydroxyquinoline is easily affected by interference from numerous drugs or medications which also fluoresce, and by interference due to nonspecific random quenching of fluorescence. In addition, 8-hydroxyquinoline is not readily loaded into cells, due to the lack of a carboxyl group.

As indicated above, currently used methods for determining magnesium levels in biological specimens are generally time consuming, inaccurate, insufficiently selective, and/or rely upon expensive instrumentation which is not likely to be available except in the largest and most highly sophisticated clinical laboratories. Furthermore, many difficulties have hindered the development of accurate and precise methods for the determination of magnesium, such as the nonspecific nature of its precipitation reactions, the susceptibility to interference from other ions, and the relatively low intensity of its spectral lines. Thus, there remains a need for methods of determining magnesium which are accurate, simple and inexpensive.

SUMMARY OF THE INVENTION

The present invention generally relates to analytical elements and methods for the selective determination of magnesium. In particular embodiments, the present invention provides methods for detecting magnesium, particularly methods for detecting $Mg^{2+}$ utilizing carboxy-quinolizines having the structure as shown in FIG. 1, Panel A.

The present invention provides methods for detecting magnesium, comprising the steps of: a) providing: i) a sample suspected of containing magnesium, and ii) a composition comprising a carboxy-quinolizine compound; b) contacting the sample with the composition to provide a complex; and c) detecting a fluorescence in the complex, wherein fluorescence indicates the presence of magnesium in the sample.

In one embodiment, the methods of the present invention provide a carboxy-quinolizine compound substituted with a functional group at the C-8 position. In particular embodiments, the functional group at the C-8 position is selected from the group consisting of chloride, —$NH_2$, —O-aryl-N—($CH_2CO_2Me$)$_2$, —CH($CO_2Me$)$_2$, —C($CO_2Me$)$_2$($CO_2Et$), p-methoxyphenyl, naphthyl, and benzo-[b]furyl.

In yet another embodiment, the carboxy-quinolizine compound is substituted with a functional group at the C-1 position. In particular embodiments, the functional group at the C-1 position is selected from the group consisting of bromide, —N($CH_2CO_2Me$)$_2$, —$CH_2$—CH($CO_2Et$)$_2$, and —CH═C—$CO_2Et$)$_2$.

In yet another embodiment, the methods of the present invention provide a carboxy-quinolizine compound substituted with a functional group at the C-1 and C-8 positions. In particular embodiments, the functional group at the C-1 position is bromide. In other embodiment, the functional group at the C-8 position is selected from the group consisting of —C($CO_2Me_2$)($CO_2Et$), —$CH_2CO_2H$ and —CH($CH_2CO_2H$)($CO_2H$). In still other embodiments, the functional group at the C-1 position is bromide, and the functional group at the C-8 position is —C($CO_2Me_2$)($CO_2Et$).

In another embodiment, the methods of the present invention provide a carboxy-quinolizine compound comprising at least two carboxyl groups. In other embodiments, the methods of the present invention provide a carboxy-quinolizine compound comprising a triacid.

In still other embodiments, the detecting step in the methods of the present invention further comprises visibly detecting the fluorescence in the complex.

In one embodiment, the methods of the present invention provide a carboxy-quinolizine compound having a $Mg^{2+}$ dissociation constant of about 1 mM. In another embodiment, the carboxy-quinolizine compound binds selectively to magnesium. In yet another embodiment, the carboxy-quinolizine compound binds selectively to magnesium ion. In yet another embodiment, the carboxy-quinolizine compound fluoresces at a wavelength greater than 500 nm.

In other embodiments, the methods of the present invention provide a sample from a subject suspected of suffering from cardiovascular disease. In another embodiment, the sample is from a subject suspected of suffering from hypertension.

Furthermore, the methods of the present invention provide a carboxy-quinolizine compound selected from the group consisting of 4-oxo-8-chloro-4H-quinolizine-3-carboxylic acid, 4-oxo-8-chloro-4H-quinolizine-3-carboxylic acid, [6,7]-benzo-4-oxo-4H-quinolizine-3-carboxylic acid, 1-bromo-4-oxo-4H-quinolizine-3-carboxylic acid, 1-[N,N-di(carboxymethyl)]-4-oxo-4H-quinolizine-3-carboxylic acid, 1-(2,2-dicarboxyvinyl)-4-oxo-4H-quinolizine-3-carboxylic acid, 1-(2,2-dicarboxyethyl)-4-oxo-4H-quinolizine-3-carboxylic acid, 8-amino-4-oxo-4H-quinolizine-3-carboxylic acid, 8-[3-N,N-di(carboxymethyl)phenoxy]-4-oxo-4H-quinolizine-3-carboxylic acid, 8-carboxymethyl-4-oxo-4H-quinolizine-3- carboxylic acid, 8-(1,2-dicarboxyethyl)-4-oxo-4H-quinolizine-3-carboxylic acid, 1-bromo-8-(1,2-dicarboxyethyl)-4-oxo-4H-quinolizine-3-carboxylic acid, 8-(4-methoxyphenyl)-4-oxo-4H-quinolizine-3-carboxylic acid, 8-(naphth-1-yl)-4-oxo-4H-quinolizine-3-carboxylic acid, and 8-(benzo[b]furyl)-4-oxo-4H-quinolizine-3-carboxylic acid.

The present invention further provides compositions suitable for selective fluorescence detection of magnesium, comprising at least one substituted carboxy-quinolizine. In preferred embodiments, the carboxy-quinolizine is a substituted 4-oxo-4H-quinolizine-3-carboxylic acid. In some preferred embodiments, the carboxy-quinolizine is substituted with a functional group at the C-1 position. In alternative preferred embodiments, the functional group at said C-1 position is selected from the group consisting of bromide, —N(CH$_2$CO$_2$Me)$_2$, —CH$_2$CH(CO$_2$Et)$_2$, and —CH=C—(CO$_2$Et)$_2$. In still further preferred embodiments, the carboxy-quinolizine is substituted with a functional group at the C-1 and C-8 positions. In yet other preferred embodiments, the functional group at said C-1 position is bromide. In additional preferred embodiments, the functional group at said C-8 position is selected from the group consisting of —C(CO$_2$Me$_2$)(CO$_2$Et), —CH$_2$CO$_2$H and —CH(CH$_2$CO$_2$H)(CO$_2$H). In some particularly preferred embodiments, the functional group at said C-1 position is bromide, and said functional group at the C-8 position is —C(CO$_2$Me$_2$)(CO$_2$Et). In additional preferred embodiments, the carboxy-quinolizine comprises at least two carboxyl groups, while in other preferred embodiments, the carboxy-quinolizine comprises a triacid. In still other particularly preferred embodiments, the carboxy-quinolizine has a dissociation constant of about 1 mM.

GENERAL DESCRIPTION OF THE INVENTION

Figure 1:
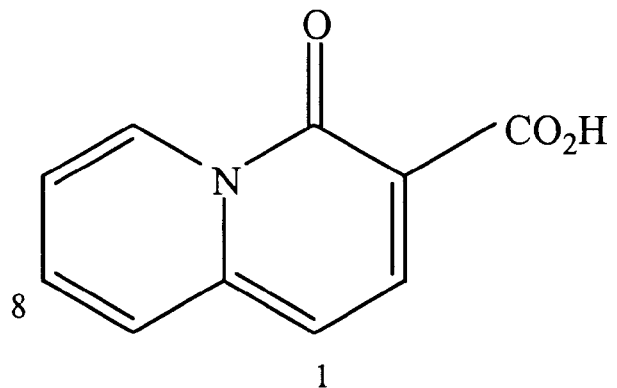
FIG. 1 provides the structure of carboxy-quinolizine and carboxy-quinolone compounds. Panel A shows the structure of 4-oxo-4H-quinolizine-3-carboxylic acid compounds used in the methods of the present invention, while Panel B shows the general structure of 4-oxo-1,4-dihydroquinoline-3-carboxylic acid compounds.
Figure 1:
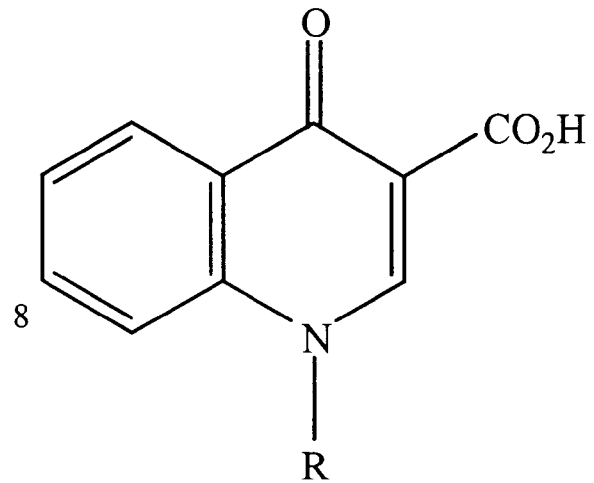

The present invention generally relates to analytical elements and methods for the selective determination of magnesium. In preferred embodiments, the present invention relates to novel fluorescent magnesium indicators. In particular embodiments, the present invention relates to carboxy-quinolizines for use as fluorescent magnesium indicators.

Fluorescence spectroscopy is a valuable tool for monitoring intracellular levels of free $Mg^{2+}$, the physiological form of magnesium. The ideal fluorescent $Mg^{2+}$ indicator possesses a number of desirable physical and fluorescence properties. First, the indicator is selective for $Mg^{2+}$ ions. Second, the dissociation constant of the indicator matches the intracellular levels of the ion to gain optimum sensitivity. Third, the fluorescence emission of the indicator ideally falls within the visible range (i.e., >500 nm), so as to prevent autofluorescence of the cell from interfering with magnesium determination. Fourth, a significant change in fluorescence occurs when binding the target $Mg^{2+}$ ion. Also, complexation of the metal ion by the indicator ideally results in a large shift of the fluorescence maximum with respect to the free indicator. This particular characteristic of the indicator allows the ion concentration to be measured as a function of the fluorescence ratio at two different wavelengths, in order to cancel out fluctuations in machine efficiency and dye concentration in the cell. Fifth, the indicator is preferably polyvalent (e.g., a polycarboxylic acid), in order for the indicator to remain in the cell during the measurement, and prevent leakage from the cell through the membrane.

Currently used fluorescent indicators for $Mg^{2+}$ are based on aminophenol triacetic acids ("APTRA") (See e.g., Levy et al., Biochemistry 27: 4041–4048 [1988]; and Raju et al., Am. J. Physiol. 256: C540–C548 [1989]). However, recent fluorescent APTRA indicators synthesized via a palladium catalyzed coupling reaction to connect the APTRA chelator and the fluorescent group exhibit a lower $Mg^{2+}/Ca^{2+}$ selectivity (Otten et al., Bioconj. Chem., 12:76–83 [2001]). The basal levels of $Ca^{2+}$ in the cell (approximately 100 nM), are several orders of magnitude lower than those found for $Mg^{2+}$, which are in the low or sub millimolar range. The dissociation constants for $Mg^{2+}$ of APTRA indicators (i.e., 1.0 to 3.9 mM) at physiological pH, correspond well with the intracellular levels of magnesium.

On the other hand, the APTRA dissociation constants for $Ca^{2+}$ of approximately 30 nM, two orders of magnitude higher than that of the basal intracellular levels for calcium. However, $Ca^{2+}$ is known to undergo dramatic increases in its intracellular levels. If such increased $Ca^{2+}$ levels approach the dissociation constant for $Ca^{2+}$ of an APTRA indicator, binding of $Ca^{2+}$ by the APTRA fluorophore will interfere with the ongoing $Mg^{2+}$ measurement. In fact, APTRA indicators have been used as high affinity $Ca^{2+}$ indicators (Saiki et al., Biochem. Bioph. Res. Co. 241: 181 [1997]; Toiyo et al., Biochem. Biophys. Res. Co. 240: 189 [1997]; and Weinberg et al., J. Clin. Invest. 100: 713 [1997]).

Quinolone compounds are known primarily as antibacterial agents (See, U.S. Pat. No. 5,037,834; EP-A-0420069; WO-A-9410163; EP-A-0343560; EP-A-0304158), antiviral agents (U.S. Pat. No. 4,959,363), and as inhibitors of 5-lipoxygenase (JP-A-02124871), cardiotonics, vasodilators and 5-$HT_3$ antagonists for the treatment of peripheral disorders associated with pain (See e.g., WO-A-9501793, GB-A-2236751, JP-A-01061461)). Fluoroquinolone antibiotics are also known to bind magnesium ion with a dissociation constant of approximately 1 mM (Okabayashi et al., Chem. Pharm. Bull. 40: 692–696 [1992]; Lecomte et al., Antimicrob. Agents Chemother. 38: 2810–2816 [1994]). However, the fluoroquinolone antibiotics of the prior art typically show a weak increase in fluorescence upon $Mg^{2+}$ complexation (i.e., approximately a factor of 2), and are not ideal fluorescent magnesium indicators (Chapman et al., Antimicrob. Agents Chemother. 32: 438–442 [1988]). None of the compounds examined by Okabayashi et al. and Lecomte et al. describes carboxy-quinolizine fluoroquinolone analogs.

Unlike other methods and indicators, the compositions and methods of the present invention provide compounds with significantly increased abilities to accurately measure intracellular and extracellular $Mg^{2+}$ levels in a wide variety of cells, tissues and fluids, even under conditions wherein calcium ion levels are elevated. In addition, the compositions of the present invention have more attractive fluorescent properties, which in some cases include an emission shift that allows for easy measurement of magnesium ion levels.

The present invention provides novel fluorescent indicators that are selective for $Mg^{2+}$. In particular, the present invention provides 4-oxo-4H-quinolizine-3-carboxylic acid derivatives which have dissociation constants that correspond excellently with commonly observed intracellular $Mg^{2+}$ levels (e.g., from 0.4 mM to 5.0 mM). The fluorophores show only slight changes in fluorescence emission due to the presence of $Ca^{2+}$, if any. The observed changes of the fluorescence emission with increasing $Mg^{2+}$ levels depend on the substitution pattern of the 4-oxo-4H-quinolizine-3-carboxylic acid ring.

The present invention also provides the first ratioable and loadable fluorescent indicators which are selective for $Mg^{2+}$.

The compound 1-[N,N-di(carboxymethyl)]-4-oxo-4H-quinolizine-3-carboxylic acid (11a) exhibits a fluorescence emission maximum at 552 nm, and comprises a triacid functionality which makes this compound loadable in cells. Thus, this compound provides a good ion-selective indicator for intracellular $Mg^{2+}$ with a 500+ nm emission wavelength. Furthermore, 1-bromo-4-oxo-4H-quinolizine-3-carboxylic acid (9a) and 1-bromo-8-(1,2-dicarboxyethyl)-4-oxo-4H-quinolizine-3-carboxylic acid (21a) display fully separated fluorescence maxima for the a free and complexed indicators. Indeed, compound (21a) was identified as the first ratioable, loadable, $Mg^{2+}$-selective, fluorescent indicator. Although it is not necessary to understand the mechanism in order to practice the present invention nor is it intended that the present invention be so limited, the presence of a bromide substituent at the 1-position of a 4-oxo-4H-quinolizine-3-carboxylic acid seems to have a significant influence on the ratioability of the fluorescent indicator. It is contemplated that other electron-withdrawing (e.g., halogen substitutents) at the 8-position will have the same effect on the fluorescent behavior of 4-oxo-4H-quinolizine-3-carboxylic acids.

The compositions and methods of the present invention are useful as diagnostic reagents for treatments that require the monitoring of physiological magnesium levels, such as in treatments for cardiovascular disease, hypertension and other diseases linked to aberrant or abnormal magnesium ion concentrations (Ford et al., Int. J. Epidemiol. 28: 645–651 [1999]; Altura et al., Cell Mol. Biol. Res. 41: 347–359 [1995]). Furthermore, the compositions of the present invention also possess useful biological activities (Li et al., J. Med. Chem. 39: 3070 [1996]; Ma et al., J. Med. Chem. 42: 4202 [1999]). For example, 4-Oxo-4H-quinolizine-3-carboxylic acids have been shown to exhibit strong activity against Gram-positive, Gram-negative and anaerobic organisms, and have been shown to be active against species that have developed, resistance to structurally related 4-quinolones.

DEFINITIONS

To facilitate the understanding of the invention, a number of terms are defined below:

As used herein, the term "carboxy-quinolizines" refers broadly to compounds containing a benzo[a]pyridine ring having carbonyl and carboxyl groups. Also, as used herein, the term "4-oxo-4H-quinolizine-3-carboxylic acid" refers to compounds having a structure according to Panel A in FIG. 1, and encompasses derivatives and analogs thereof.

As used herein, the term "carboxy-quinolones" refers broadly to compounds containing a benzo[b]pyridine ring having carbonyl and carboxyl groups. Also, as used herein, the term "4-oxo-1,4-dihydroquinoline-3-carboxylic acid" refers to compounds having a structure according to Panel B in FIG. 1, and encompasses derivatives and analogs thereof. In this Figure, "R" is an alkyl group.

As used herein, the term "fluorescence" or "fluorescent" refer to a type of luminescence in which an atom or molecule emits visible radiation in passing from a higher to a lower electronic state. The time interval between absorption and emission energy is typically $10^{-8}$ to $10^{-3}$ seconds.

As used herein, the term "fluorescent magnesium indicators" refers to compounds which complex magnesium ions and fluoresce upon complexation. In particularly preferred embodiments, the compounds of the present invention provide means for the selective detection of magnesium (e.g., $Mg^{2+}$) in samples.

As used herein, the term "complex" refers to a compound produced by the binding of a metal ion (e.g., $Mg^{2+}$, $Ca^{2+}$, $Zn^+$, $Cu^{2+}$, $Fe^{3+}$, etc.) to a complexing agent.

As used herein, the term "ion" refers to an atom, radical, molecule or a compound that has lost or gained one or more electrons, resulting in an electric charge. Positively charged ions are "cations" and negatively charged ions are "anions."

As used herein, the term "fluorescent magnesium indicators" refers to compounds which complex magnesium ions and fluoresce upon complexation. In particularly preferred embodiments, the compounds of the present invention provide means for the selective detection of magnesium (e.g., $Mg^{2+}$) in samples.

As used herein, the term "complex" refers to a compound produced by the binding of a metal ion (e.g., $Mg^{2+}$, $Ca^{2+}$, $Zn^+$, $Cu^{2+}$, $Fe^{3+}$, etc.) to a complexing agent.

As used herein, the term "ion" refers to an atom, radical, molecule or a compound that has lost or gained one or more electrons, resulting in an electric charge. Positively charged ions are "cations" and negatively charged ions are "anions."

As used herein, the term "carboxylic acids" refers to a broad class of carboxyl-containing (—$CO_2H$) organic compounds.

As used herein, the term "alcohol" refers to a broad class of hydroxyl-containing (—OH) organic compounds.

As used herein, the term "amines" refers to a broad class of amino-containing (—$NH_2$) organic compounds.

As used herein, the term "alkyl" refers to an unsubstituted or substituted saturated hydrocarbon chain comprising 1 to 8 carbon atoms, preferably from 1 to 4 carbon atoms. Also, as referred to herein, a "lower alkyl" refers to an unsubstituted or substituted saturated hydrocarbon chain comprising 1 to 6 carbon atoms, preferably 1 to 4 carbon atoms.

As used herein, the term "alkenyl" refers to an unsubstituted or substituted hydrocarbon chain having from 2 to 8 carbon atoms, preferably from 2 to 4 carbon atoms, and having at least one olefinic double bond (including but not limited to vinyl, allyl and butenyl).

As used herein, the term "alkoxy" refers to a hydrocarbon chain comprising an oxygen atom. Also, as used herein, the term "alkoxy phenyl" refers to an alkoxy group substituted with an aromatic group (e.g., p-methoxyphenyl).

As used herein, the term "alkylamino" refers to an amino group comprising one or two alkyl substituents (i.e., —N-alkyl). Also, as used herein, the term "arylamino" refers to an amine substituted with an aryl group (e.g., NH-aryl).

As used herein, the term "arylalkyl" refers to an alkyl substituted with an aryl group.

As used herein, the term "aryloxy" refers to an oxygen atom substituted with an aryl group.

As used herein, the term "halo," "halogen," and "halide" refers to a fluoride, chloride, bromide, iodide, or a combination thereof. Preferred halides are chlorides and bromides.

As used herein, the terms "aryloxy" and "O-aryl" refer to an oxygen atom having an aryl substituent.

As used herein, the terms "C-1 position" and "C-8 position" refer to carbons at the 1 and 8 positions of the 4-oxo-4H-quinolizine-3-carboxylic acid ring, respectively, as shown in FIG. I.

As used herein, the term "emission shift" refers to the shift in fluorescence emission maximum to a longer or shorter wavelength in comparison to the free indicator.

As used herein, the term "dissociation constant" refers to the $K_a$ and $K_b$ values of acids and bases, which are constants that indicate the relative strength of acids and bases, respectively.

As used herein, the term "sample" is used in its broadest sense and encompasses biological and environmental samples. Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. In addition, this term encompasses all types of samples obtained from humans and other animals, including but not limited to, body fluids such as urine, blood, fecal matter, cerebrospinal fluid (CSF), semen, and saliva, as well as solid tissue. These examples are not to be construed as limiting the sample types applicable to the present invention.

DETAILED DESCRIPTION OF THE INVENTION

The present invention relates to carboxy-quinolizine magnesium indicators, and more particularly, to 4-oxo-4H-quinolizine-3-carboxylic acid derivatives for use as fluorescent magnesium indicators. The Detailed Description of the Invention is divided into the following sections: I) 4-Oxo-4H-Quinolizine-3-Carboxylic Acids; II) Fluorescent Properties of 4-Oxo-4H-Quinolizine-3-Carboxylic acid Derivatives; and III) Use of 4-Oxo-4H-Quinolizine-3-Carboxylic acid Derivatives.

I. 4-oxo-4H-Quinolizine-3-carboxylic Acids

The present invention provides carboxy-quinolizines for use as novel fluorescent magnesium indicators, and encompasses but is not limited to 4-oxo-4H-quinolizine-3-carboxylic acid compounds having the structure shown in FIG. 1.

The compounds may comprise substituent groups selected from the group consisting of hydrogen, alkyls, alkenyls, alkoxys, halogens, esters, phenyl esters, amides, esters, aryls, naphthyls and benzo[b]furyl groups. However, it is not intended that the compounds of the present invention be limited to particular functional groups. Indeed, other functional groups such as aliphatic groups, phenyl groups, thiol groups, nitro groups, acyl groups, acetyl groups, acetate groups, benzyloxy groups, oxo groups, naphthyloxy groups, naphthylthio groups, acetonitrile groups, acetamide groups, acetoxy groups, benzyl groups, benzoyl groups, sulfonic acid groups and other functional groups are contemplated to be within the scope of the present invention.

Figure 2:
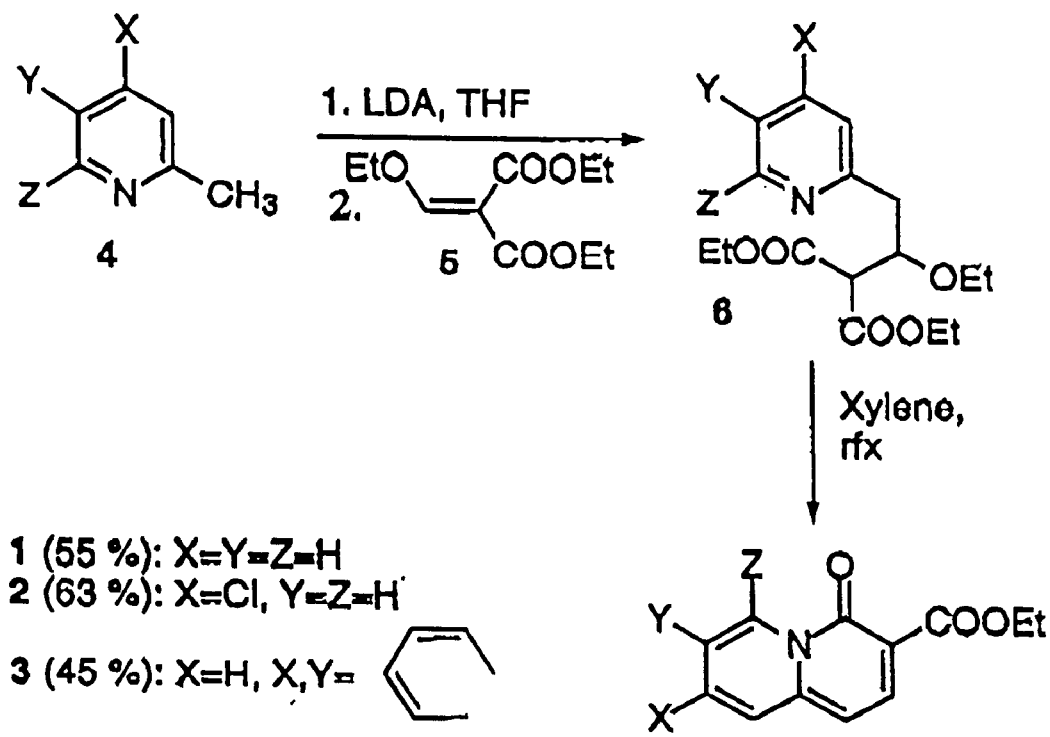
FIG. 2 shows a schematic synthesis of precursor ethyl esters of 4-oxo-4H-quinolizine-3-carboxylic acid used in the methods of the present invention.

In general, esters of 4-oxo-4H-quinolizine-3-carboxylic acids can be synthesized by a thermal ring closure reaction of a 2-picoline Michael type-adduct and diethyl ethoxymethylenemalonate, as shown schematically in FIG. 2. The ethyl esters of 4-oxo-4H-quinolizine-3-carboxylic acids (1), (2), and (3) were synthesized in two steps starting from the corresponding commercially available 2-picolines or 2-methylquinoline (4) (See, FIG. 2). The first step is a Michael-type reaction of the lithiated 2-picoline anion (4)-Li (generated in situ with lithium diisopropyl amide [LDA]) with diethyl ethoxymethylenemalonate (5) ("EMME"). Subsequent ring closure of the Michael adducts (6) was effected in refluxing xylene, after which the desired ethyl esters of 4-oxo-4H-quinolizine-3-carboxylic acids (1), (2), and (3) were obtained as crystalline materials in moderate to good yields.

A. Electrophilic Aromatic Substitution

Figure 3:
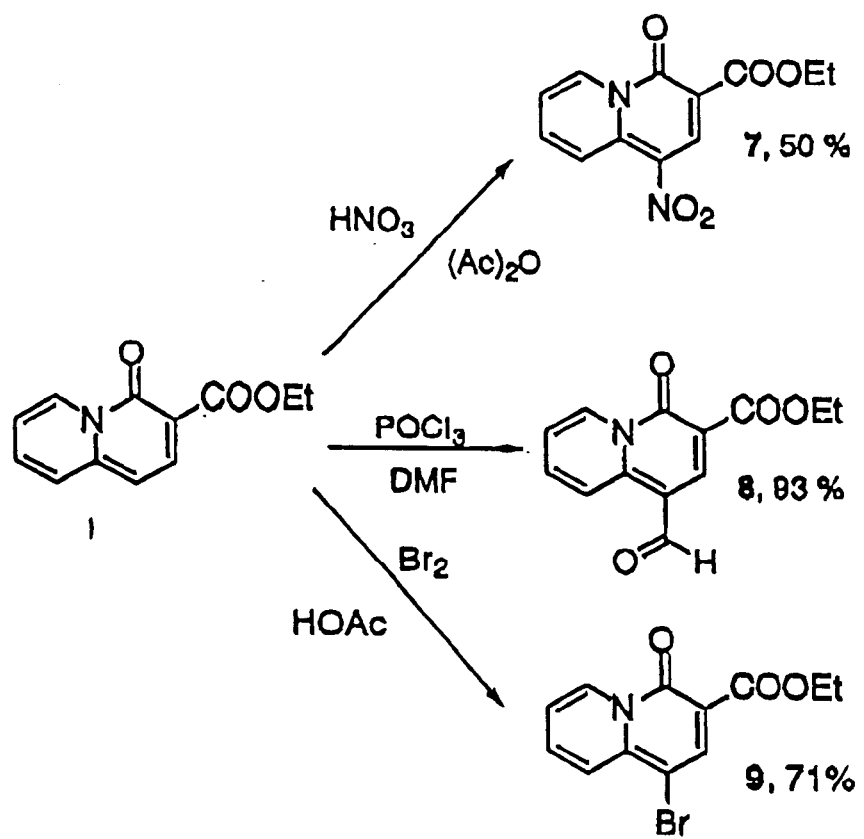
FIG. 3 shows a schematic electrophilic aromatic substitution of ethyl esters of 4-oxo-4H-quinolizine-3-carboxylic acids precursors used in the methods of the present invention.

The introduction of functional groups into compound (1) is readily achieved by a regioselective, electrophilic aromatic substitution at the 1-position, as shown schematically in FIG. 3. Thus, treatment of compound (1) with $HNO_3$ in acetic anhydride resulted in the isolation of ethyl-1-nitro-4-oxo-4H-quinolizine-3-carboxylate (7) at a 50% yield. Similarly, formylation of (1) with a Vilsmeier-Haack reaction gave ethyl 1-formyl-4-oxo-4H-quinolizine-3-carboxylate (8) in 93% yield. The bromination of compound (2) was achieved by treatment with $Br_2$ in acetic acid to give compound (9) in 71% yield.

Figure 4:
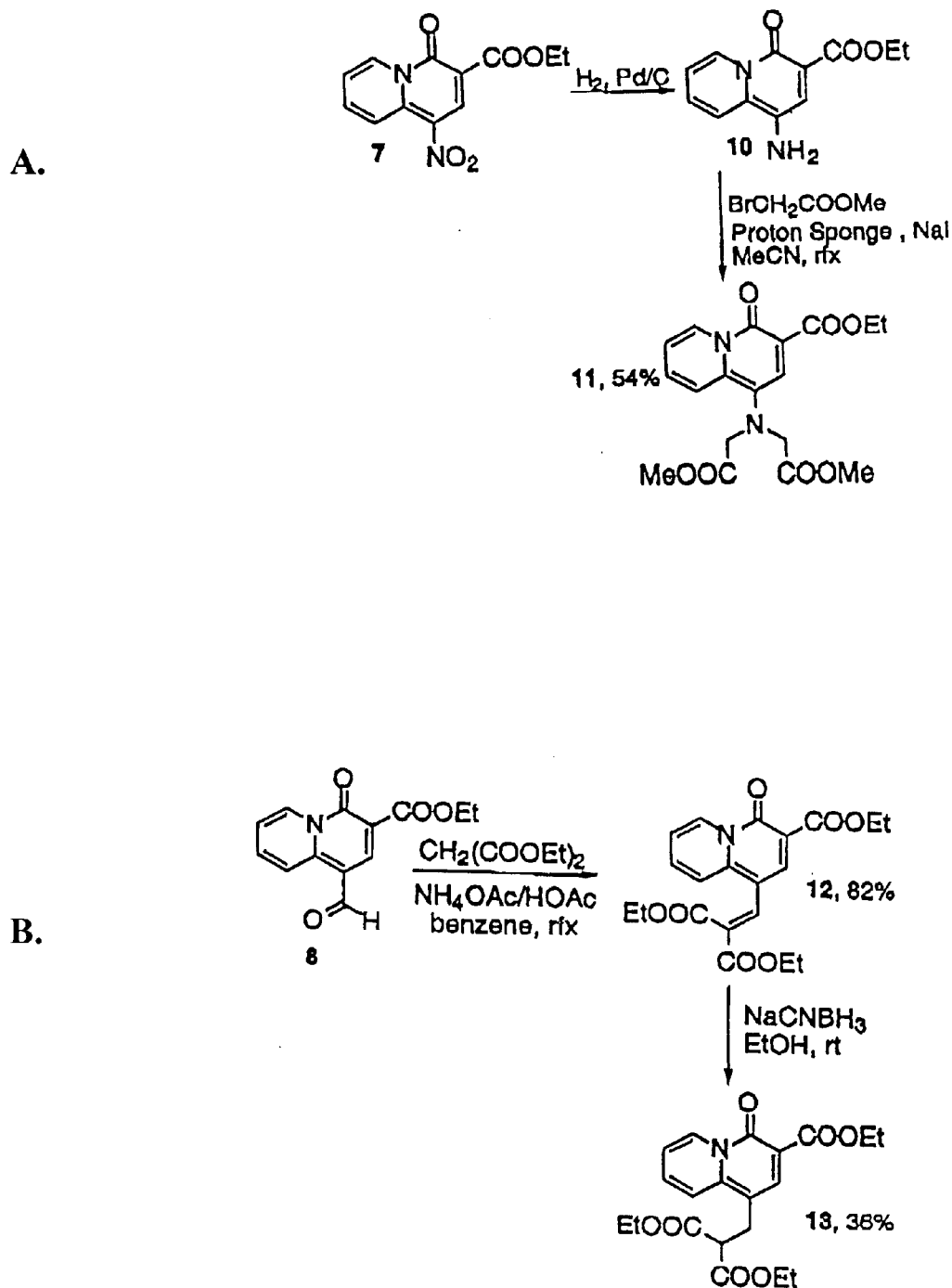
FIG. 4, Panels A and 4B shows two schematic syntheses of the compounds used in the methods of the present invention.

The nitro and formyl groups in compounds (7) and (8), respectively, are excellent starting points for the introduction of two extra carboxylic acid groups in the 4-oxo-4H-quinolizine-3-carboxylic acid structure, to give a polyvalent fluorophore, as shown schematically in FIG. 4A. The reduction of the nitro group in compound 7 was accomplished by palladium-catalyzed hydrogenation to give amine (10). Alkylation of amine (10) with methyl bromoacetate in refluxing acetonitrile in the presence of NaI and PROTON SPONGE®, resulted in the formation of triester (11) in 54% yield from compound (7).

An aldol condensation reaction of aldehyde (8) with diethyl malonate led to the production of diethyl methylenemalonate triester (12), as schematically shown in FIG. 4B. The saturated derivative (13) was obtained by a selective reduction of the double bond in compound (12) with $NaCNBH_3$ in ethanol.

B. Nucleophilic Substitution of the Cl Substituent

Figure 5:
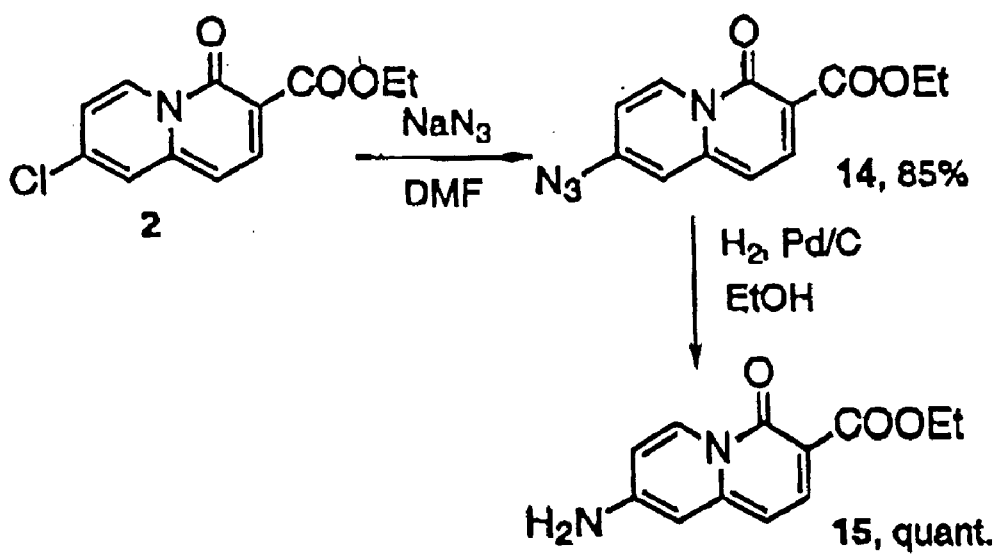
FIG. 5 shows a schematic nucleophilic substitution of ethyl esters of 4-oxo-4H-quinolizine-3-carboxylic acids of the present invention.

The chloro substituent of ethyl 8-chloro-4-oxo-4H-quinolizine-3-carboxylate (2) is easily substituted with a variety of nucleophiles, and may be coupled with boronates in palladium-catalyzed coupling reactions (i.e., Suzuki coupling). This reactivity of (2) offers another possibility to introduce functionality into the 4-oxo-4H-quinolizine-3-acid structure. Treatment of compound (2) with $NaN_3$ in DMF at 40° C. resulted in clean replacement of the Cl substituent by an azido group, to give compound (14) in 85% yield, as shown schematically in FIG. 5. Reduction of the azido group by palladium-catalyzed hydrogenation gave the corresponding amine (15) in almost quantitative yield. However, alkylation of compound (15) with methyl bromoacetate (i.e., analogous to the preparation of (10)) failed. Although it is not necessary to understand the mechanism of the present invention nor is it intended that the present invention be so limited, it is believed that the strong electron deficient nature of the heterocyclic system, which facilitates the replacement of the chloro substituent in (2), decreases the nucleophilic character of the amine substituent. An alternative approach to substitute the chloro substituent in compound (2) with diethyl iminoacetate [$HN(CH_2COOMe)_2$] also failed, presumably because of a lack of sufficient nucleophilic character of the amine.

Figure 6:
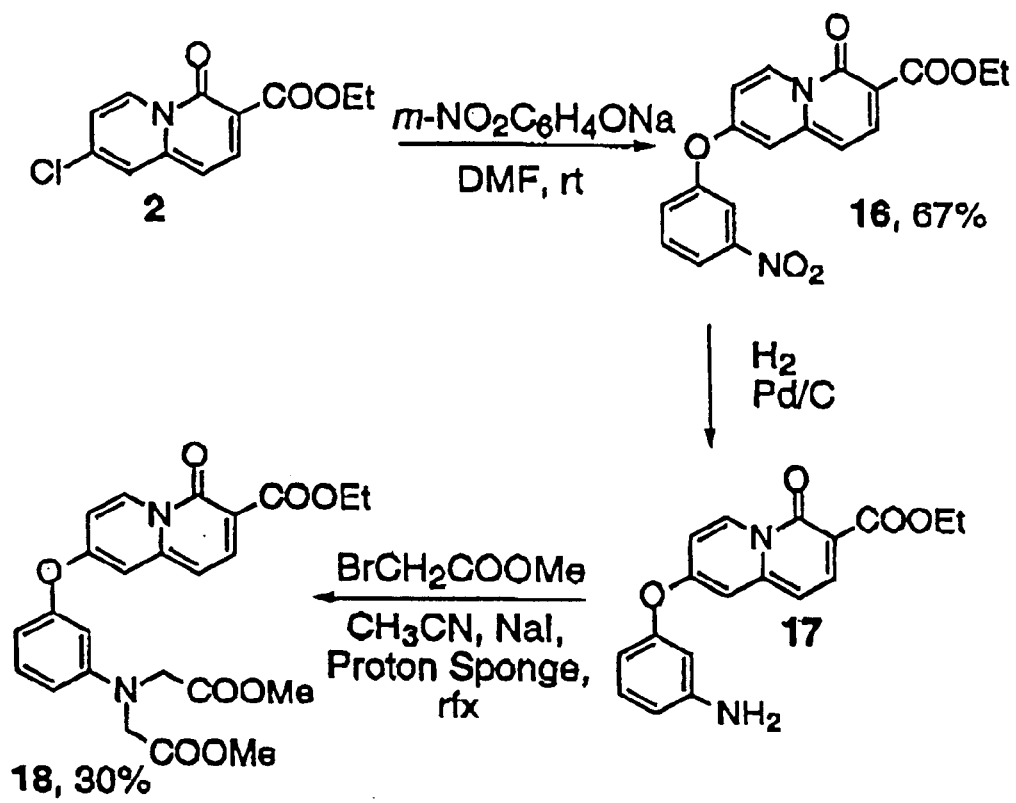
FIG. 6 shows a schematic synthesis of the compounds of the present invention.

The reaction of compound (2) with the anion of m-nitrophenol, generated in situ by deprotonation of the phenol with NaH, resulted in substitution of the chloro substituent with an oxygen nucleophile to give the ether (16) in a yield of 67%. Reduction of the nitro group of (16) resulted in the amine (17). A subsequent alkylation reaction with the crude amine and methyl bromoacetate resulted in the isolation of triester (18) in 30% yield over two steps, as shown in FIG. 6.

Figure 7:
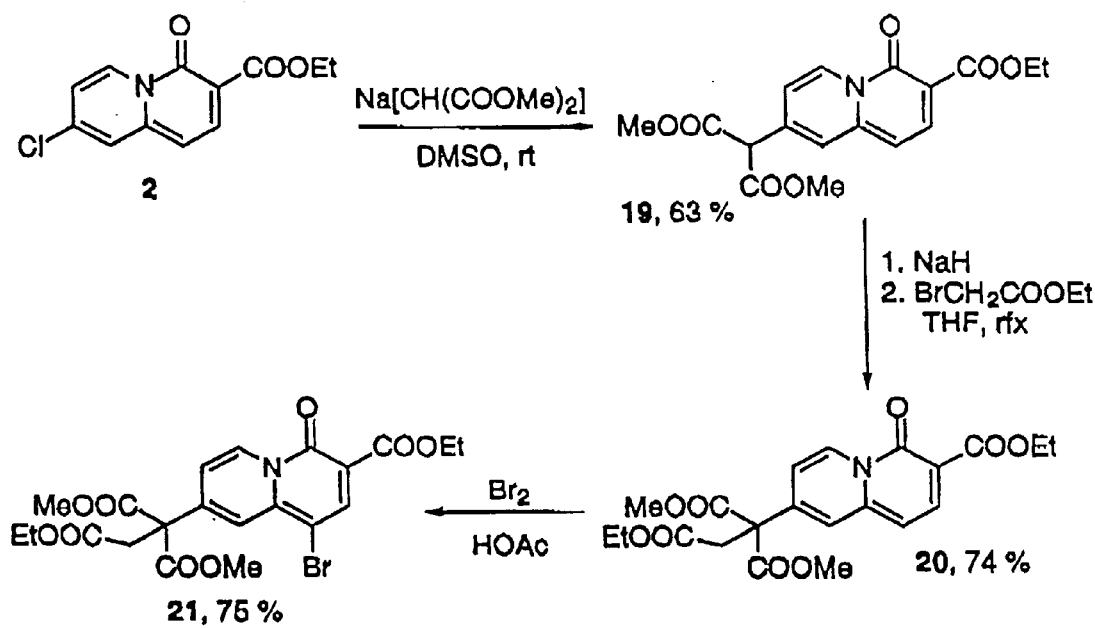
FIG. 7 shows another schematic synthesis of the compounds of the present invention.

The chloro substituent of (2) can also be replaced by a carbon nucleophile. Thus, the reaction of (2) with the anion of diethyl malonate in DMSO led to the formation of triester (19) which was isolated in 63% yield, as shown schematically in FIG. 7. At least two equivalents of the malonate anion were found to be required for complete consumption of (2), most likely as a result of deprotonation of the more acidic substitution product (19) by a malonate anion, although it is not necessary to understand the mechanism in order to practice the present invention, and it is not intended that the present invention be so limited. The remaining acidic proton of (19) was readily abstracted by NaH in THF, and alkylation of the corresponding anion with ethyl bromoacetate afforded tetraester (20) in 74% yield. Bromination of compound (20) was achieved by reaction with $Br_2$ in acetic acid, to give compound (21) in 75% yield, as shown schematically in FIG. 7.

Figure 8:
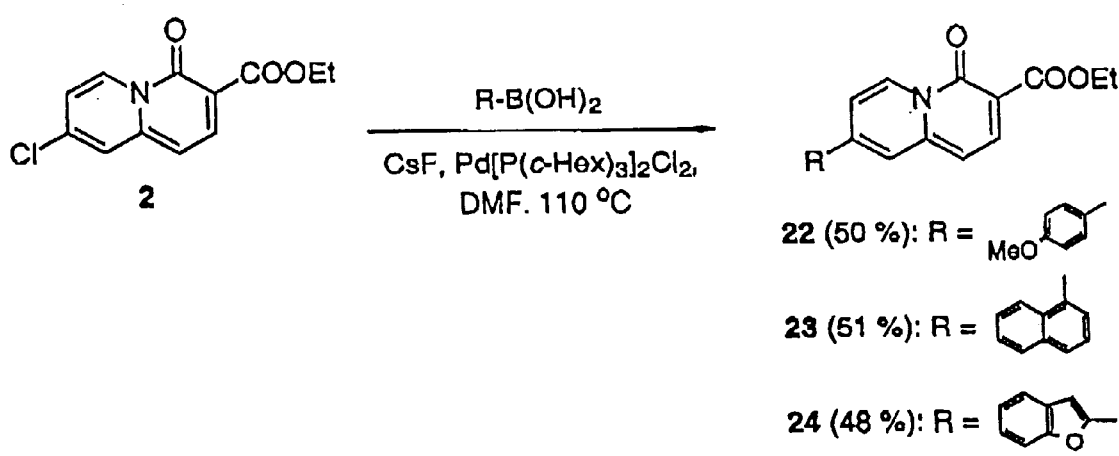
FIG. 8 shows a schematic Suzuki coupling reaction of ethyl esters of 4-oxo-4H-quinolizine-3-carboxylic acids of the present invention.

Although it is not necessary to understand the mechanism in order to practice the present invention nor is it intended that the present invention be so limited, it is believed that the extension of the π-system of the 4-oxo-4H-quinolizine-3-carboxylic acid structure shifts the fluorescence emission maximum to longer wavelengths, possibly to the visible light range. One methodology for substituting the chlorine atom at the 8-position of compound (2) with an aromatic carbon nucleophile involves a palladium-catalyzed coupling reaction of the electron poor aryl chloride (2) with an organoboron species (i.e., Suzuki reaction). However, the two phase system consisting of an organic solvent and an aqueous base usually applied for Suzuki coupling could not be used because of the presence of the ester group in compound (2). Therefore, base free reaction conditions described by Shen (Shen, Tetrahedron Lett. 38: 5575 [1997]) were followed for the Suzuki reactions described herein, which gave the coupling products in good yields. Using this procedure, a p-methoxyphenyl, a naphth-1-yl, and a benzo-[6,7]-furyl group were substituted at the 8-position of the parent 4-oxo-4H-quinolizine-3-carboxylate compound, as shown schematically in FIG. 8.

C. Saponification

Figure 9:
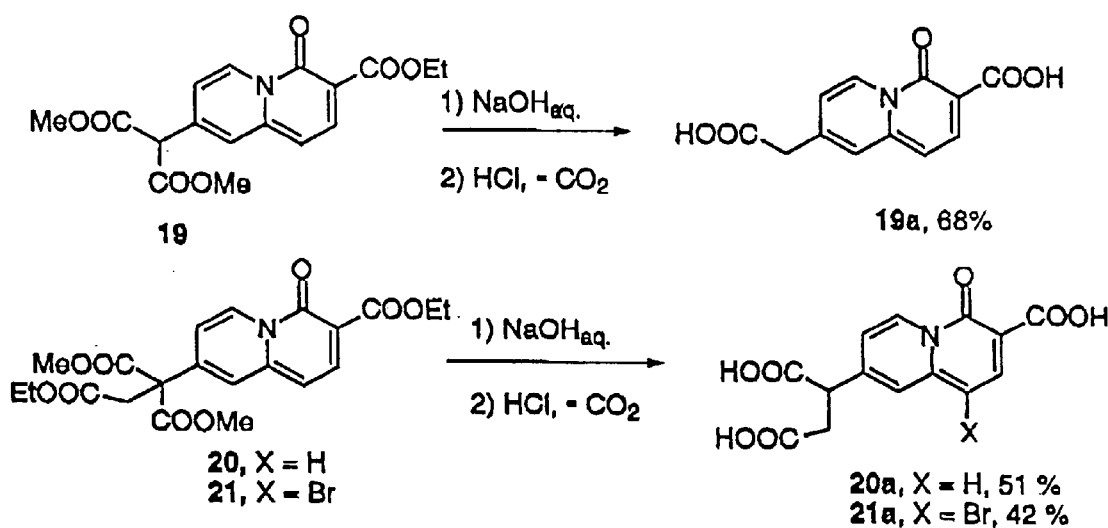
FIG. 9 shows another schematic synthesis of the compounds of the present invention.

Compounds (1–3), (9), (11–13), (15), and (18–24) were saponified, followed by acidic work-up to isolate the corresponding polyacids in the protonated form (i.e., compounds (1a–3a), (9a), (11a–13a), (15a), and (18a–24a)). The saponification products of triester (19) and tetraesters (20) and (21) decarboxylated rapidly at low pH and 5° C., and the resulting diacid (19a) and triacids (20a) and (21a) were isolated accordingly, as shown schematically in FIG. 9.

II. Fluorescent Properties of 4-oxo-4H-Quinolizine-3-carboxylic Acids

The emission and excitation fluorescence spectra of the compounds of the present invention (e.g., (1a–3a), (9a), (11a–13a), (15a), and (18a–24a)) were recorded using a 0.5 to 1.0 μM solution of the chelator buffered at pH 7.2. The solutions also contained 120 mM KCl and 20 mM NaCl to mimic the ionic strength of the intracellular medium. These solutions were titrated with stock solutions of $MgCl_2$ containing an equimolar concentration of the 4-oxo-4H-quinolizine carboxylic acids to cancel out dilution effects during the titration. After each titration step, the emission and excitation fluorescence spectra were recorded. The absorption maxima and the fluorescence emission maxima of 4-oxo-4H-quinolizine compounds are shown in Table 1. The apparent dissociation constants of indicators for $Mg^{2+}$ were determined from the fluorescence spectra as originally described by Grynkiewicz et al. (Grynkiewicz et al., J. Biol. Chem. 260: 3440–3450 [1985]). Solutions of the fluorophores in the buffer were found to be stable for at least 9 months at 4° C.

TABLE 1

Spectroscopic data and Kd values.

| Compound | A (nm)[a] | Emission (nm)[b] | $K_d$ (mM) |
|---|---|---|---|
| 4-Oxo-4H-Quinolizine-3-Carboxylic Acid (1a) | 385 | 435 → 408 | 1.1 |
| 4-Oxo-8-Chloro-4H-Quinolizine-3-Carboxylic Acid (2a) | 391 | 445 → 418 | 5.0 |
| [6,7]-Benzo-4-Oxo-4H-Quinolizine-3-Carboxylic acid (3a) | 410 | 485 → 467 | 4.6 |
| 1-Bromo-4-Oxo-4H-Quinolizine-3-Carboxylic Acid (9a) | 403 | 460 → 442 | 1.5 |
| 1-[N,N,-Di(Carboxymethyl)]-4-Oxo-4H-Quinolizine-3-Carboxylic Acid (11a) | 410 | 552 → 548 | 0.5 |
| 1-(2,2-Dicarboxyvinyl)-4-Oxo-4H-Quinolizine-3-Carboxylic Acid (12a) | 400 | 466 → 461 | 0.4 |
| 1-(2,2-Dicarboxyethyl)-4-Oxo-4H-Quinolizine-Carboxylic Acid (13a) | 395 | 456 → 429 | 0.5 |
| 8-Amino-4-Oxo-4H-Quinolizine-3-Carboxylic Acid (15a) | 385 | 406 → 396 | 1.1 |
| 8-[3-(N,N-Di(Carboxymethyl)phenoxyl]4-Oxo-4H-Quinolizine-3-Carboxylic Acid (18a) | 370 | 412 → 402 | 1.0 |
| 8-[Carboxymethyl]-4-Oxo-4H-Quinolizine-3-Carboxylic Acid (19a) | 380 | 432 → 410 | 1.1 |
| 8-(1,2-Dicarboxyethyl)-4-oxo-4H-Quinolizine-3-Carboxylic Acid (20a) | 390 | 432 → 411 | 0.4 |
| 1-Bromo-8-(1,2-Dicarboxyethyl)-4-Oxo-4H-Quinolizine-3-Carboxylic Acid (21a) | 407 | 463 → 437 | 0.7 |
| 8-(4-Methoxyphenyl)-4-Oxo-4H-Quinolizine-Carboxylic Acid (22a) | 406 | 470 → 444 | 1.2 |
| 8-(Naphth-1-yl)-4-Oxo-4H-Quinolizine-3-Carboxylic Acid (23a) | 386 | 490 → 456 | 1.5 |
| 8-(Benzo[b]furyl)-4-Oxo-Quinolizine-3-Carboxylic Acid (24a) | 440 | 496 → 459 | 1.3 |

[a]Absorption maximum of the free indicator.
[b]An arrow denotes a shift of the fluorescence maximum upon saturation of the indicator.

Figure 10:
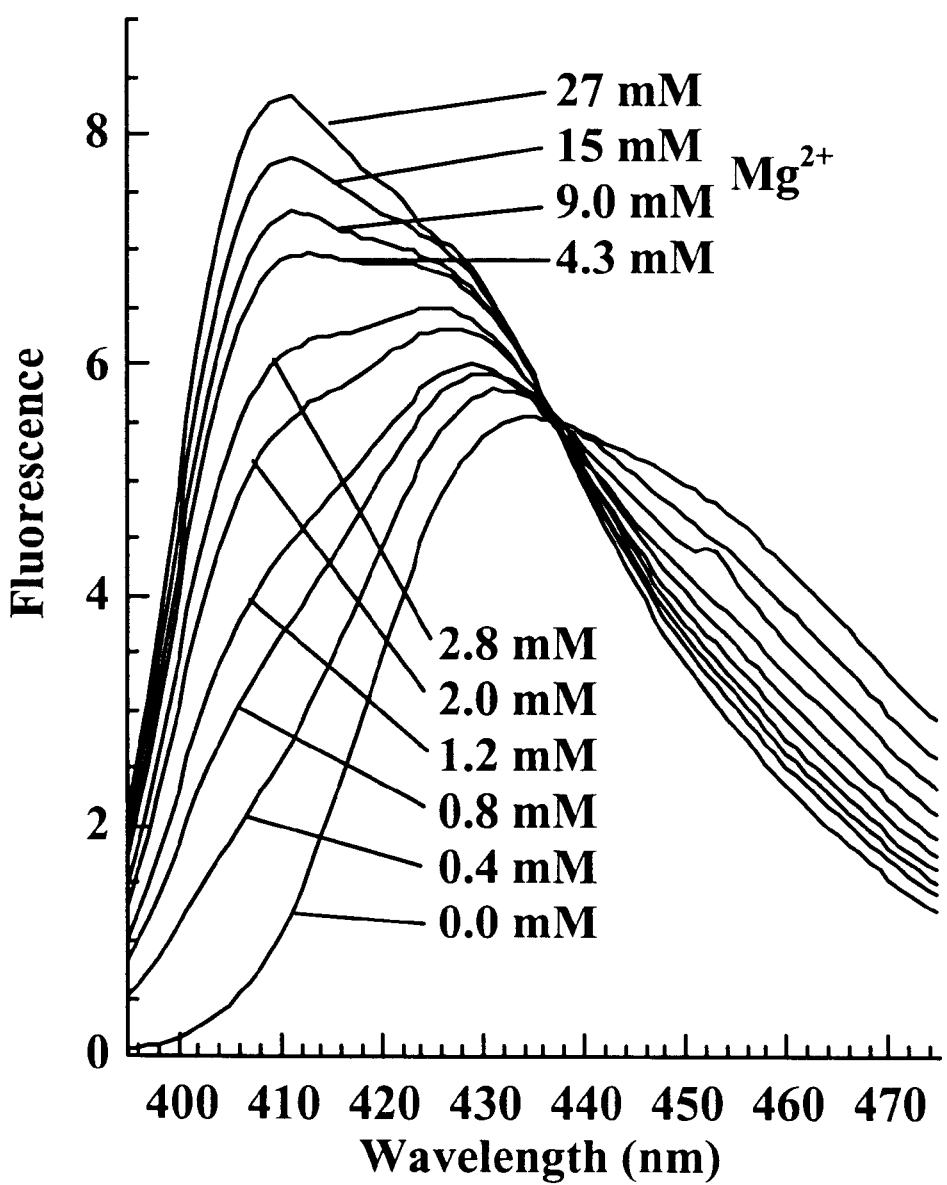
FIG. 10 shows the fluorescence emission spectrum of 4-oxo-4H-quinolizine-3-carboxylic acid (1a) upon complexation with $Mg^{2+}$.
Figure 11:
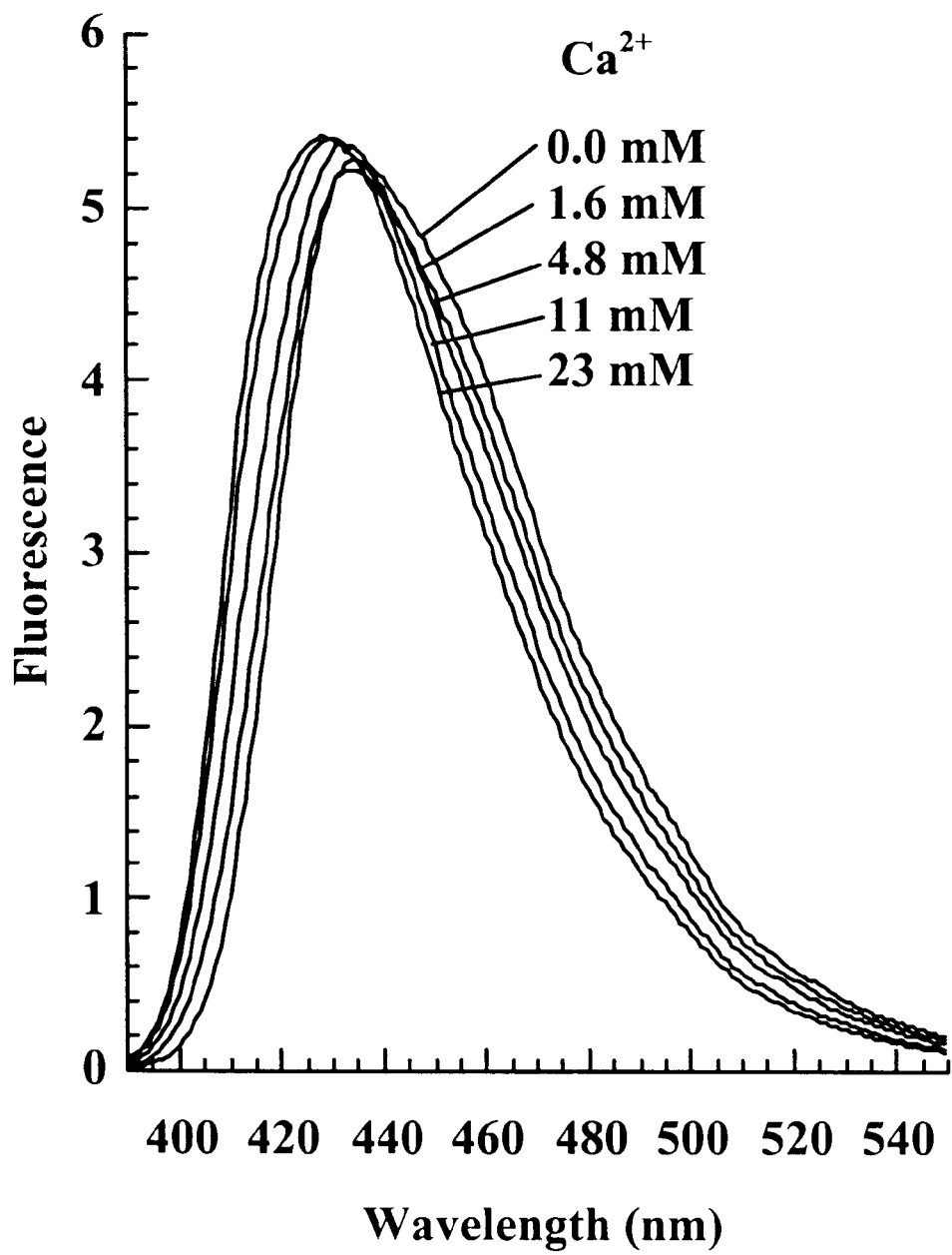
FIG. 11 shows the fluorescence emission spectrum of 4-oxo-4H-quinolizine-3-carboxylic acid (1a), upon complexation with $Ca^{2+}$.
Figure 12:
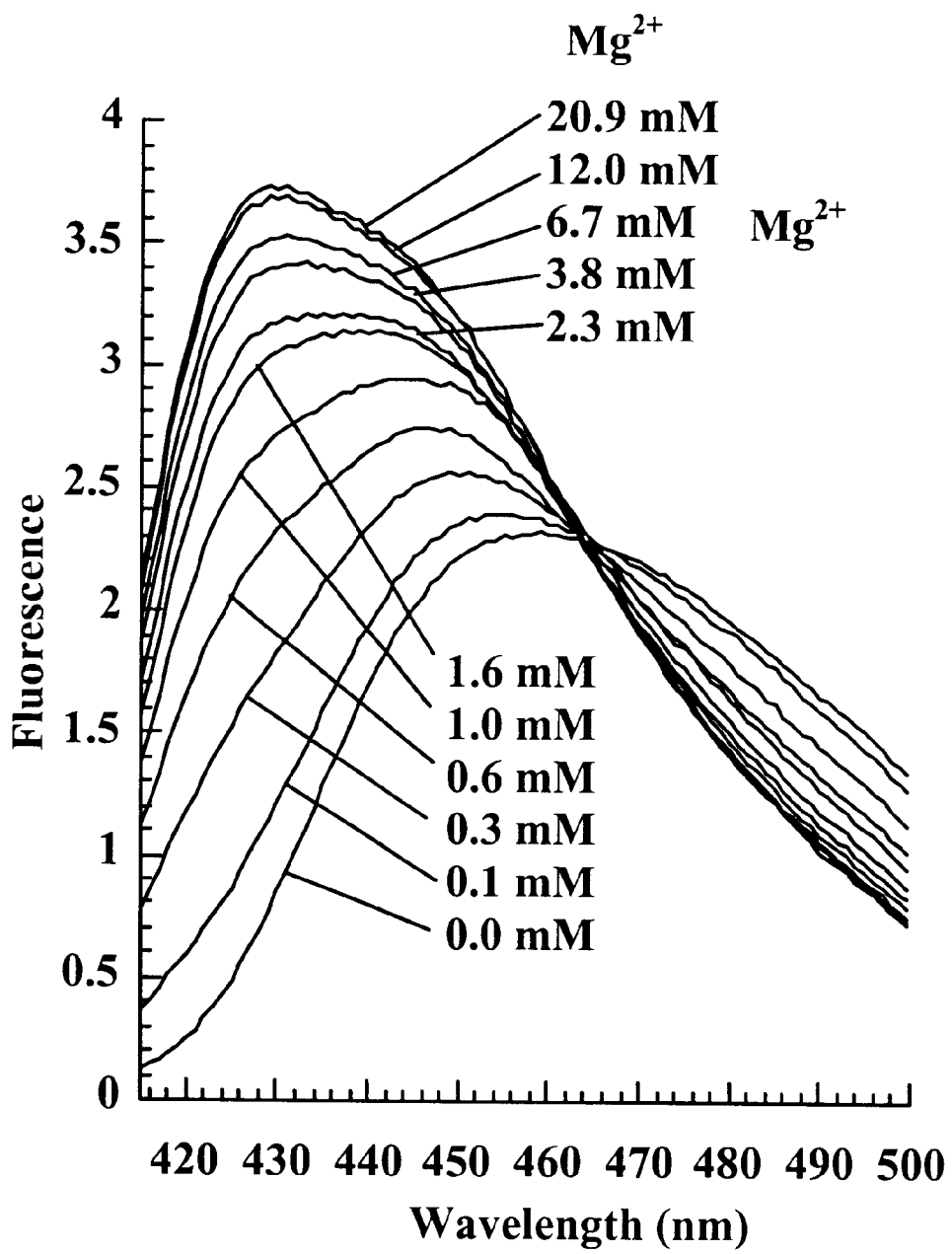
FIG. 12 shows the fluorescence emission spectrum of 1-(2,2-dicarboxyethyl)-4-oxo-4H-quinolizine-3-carboxylic acid (i.e., compound 13a), upon complexation with $Mg^{2+}$.

In most cases, a bathochromic shift of the fluorescence emission was found to occur upon binding $Mg^{2+}$ by the indicator. The observed shifts range from 4 nm for 1-[N,N-di(carboxymethyl)]-4-oxo-4H-quinolizine-3-carboxylic acid (11a) to 37 nm for 8-benzo[b]furyl)-4-oxo-4H-quinolizine-3-carboxylic acid (24a). The parent compound 4-oxo-4H-quinolizine-3-carboxylic acid (1a) displays a bathochromic shift of 23 nm when saturated with $Mg^{2+}$, with a crossover point at 437 nm (See, FIG. 10). FIG. 11 shows the fluorescent response of 4-oxo-4H-quinolizine-3-carboxylic acid (1a) to increasing $Ca^{2+}$ concentrations. As shown in FIG. 11, intracellular $Ca^{2+}$ levels in the nanomolar to submicromolar range do not affect the fluorescence emission of 4-oxo-4H-quinolizine-3-carboxylic acid (1a). For most other 4-oxo-4H-quinolizine-3-carboxylic acids, the $Mg^{2+}$-induced fluorescence emission spectra of the free indicator and the $Mg^{2+}$-bound indicator largely overlap. The fluorescent response of the alkyl-substituted indicator 1-(2,2-dicarboxyethyl)-4-oxo-4H-quinolizine-3-carboxylic acid (13a), a triacid in which a 2,2-dicarboxyethyl substituent has been introduced at the 1-position to enhance water solubility, is almost identical to that observed for 4-oxo-4H-quinolizine-3-carboxylic acid (1a), as shown in FIG. 12.

Figure 13:
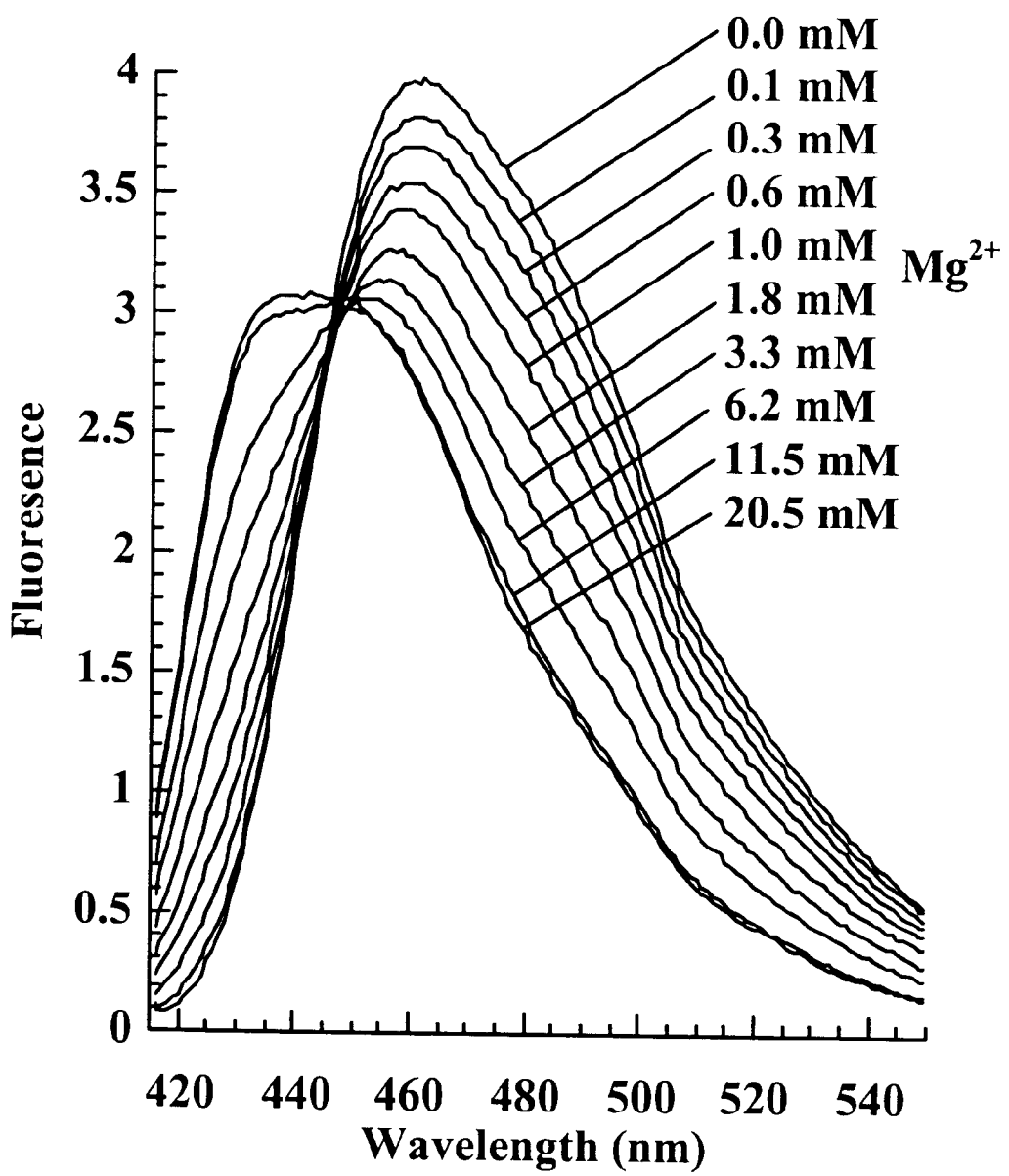
FIG. 13 shows the fluorescence emission spectrum of 1-bromo-4-oxo-4H-quinolizine-3-carboxylic acid (9a), upon complexation with $Mg^{2+}$.
Figure 14:
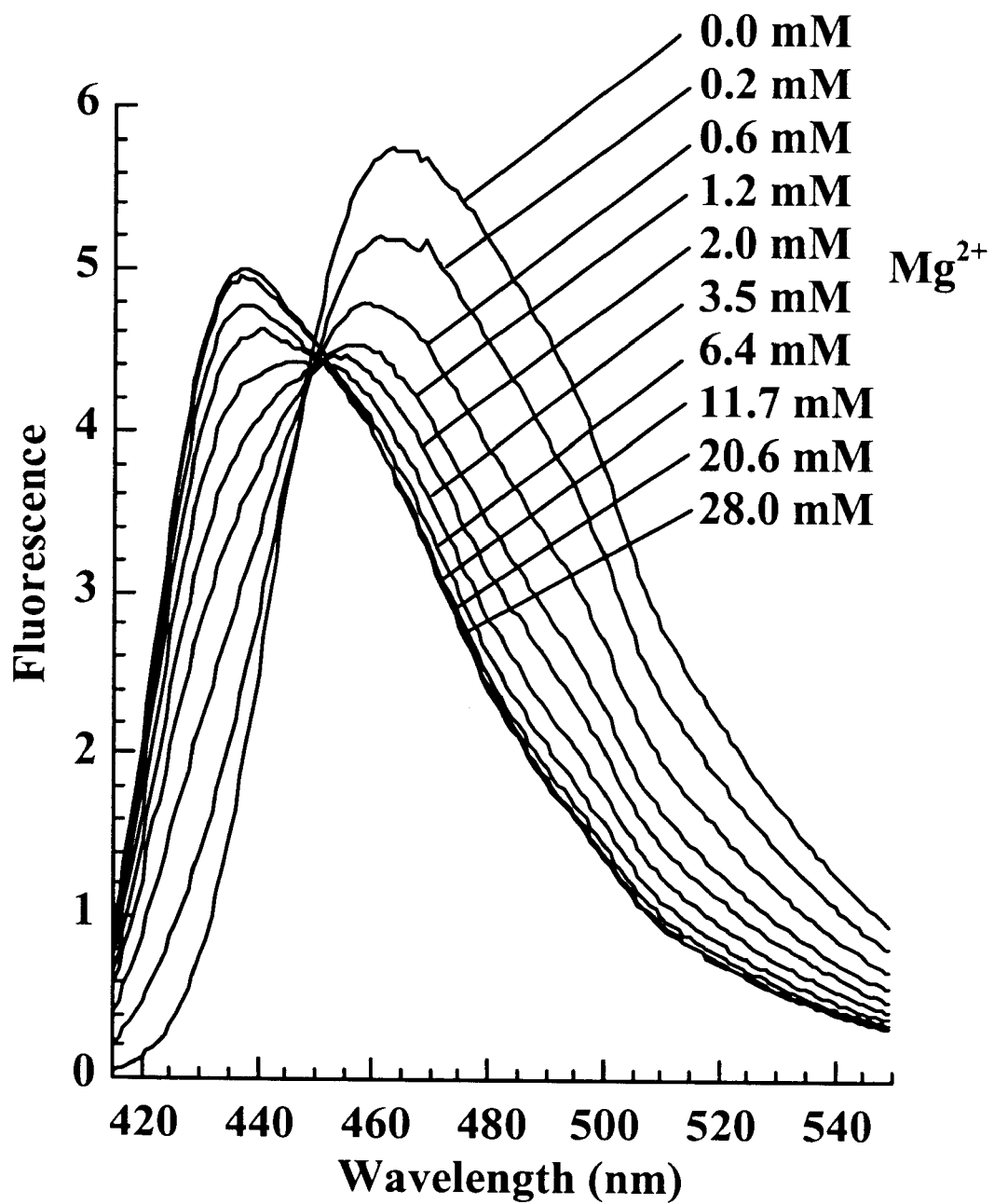
FIG. 14 shows the fluorescence emission spectrum of 1-bromo-8-(1,2-dicarboxyethyl)-4-oxo-4H-quinolizine-3-carboxylic acid (21a), upon complexation with $Mg^{2+}$.
Figure 15:
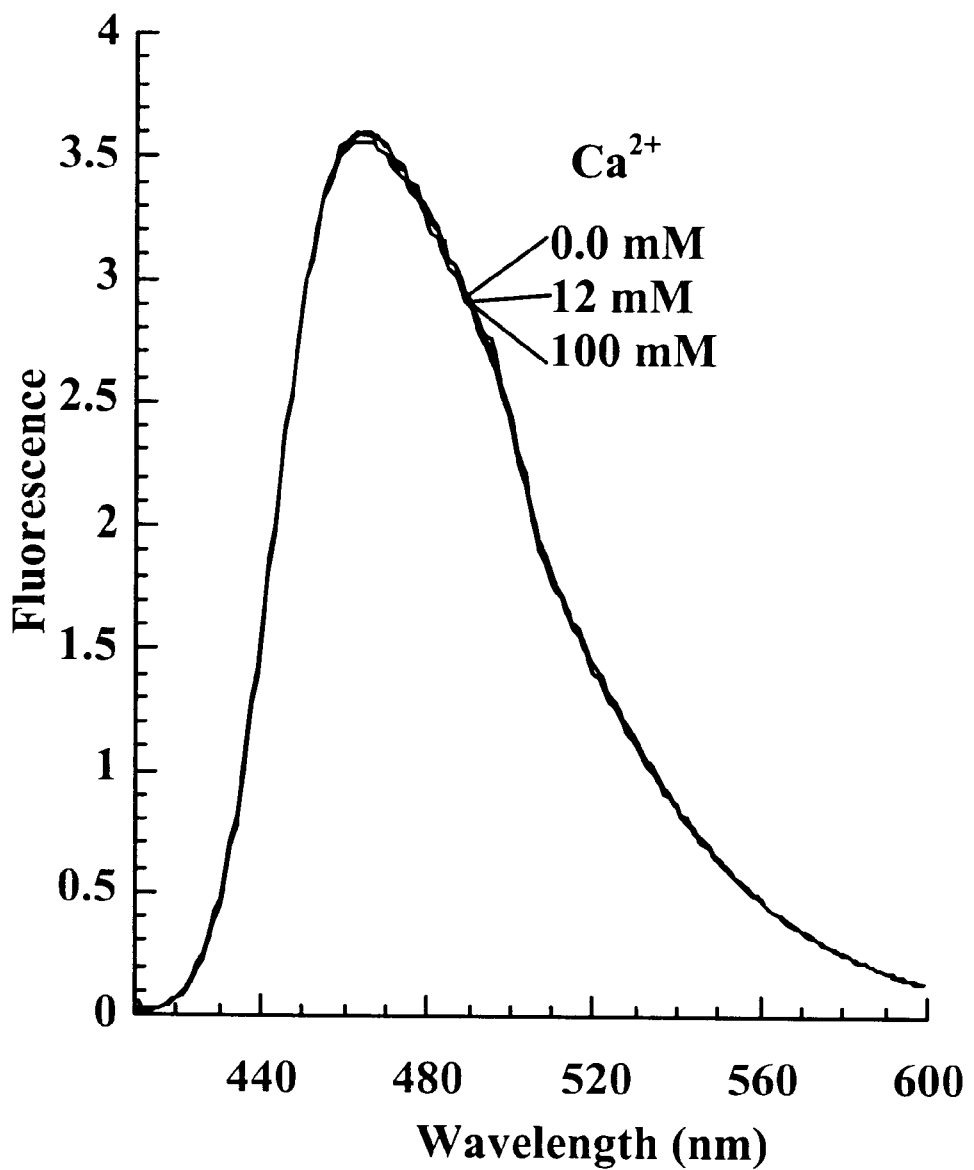
FIG. 15 shows the fluorescence emission of 1-bromo-8-(1,2-dicarboxyethyl)-4-oxo-4H-quinolizine-3-carboxylic acid (21a), upon complexation with $Ca^{2+}$.

The presence of a bromine substituent at the 1-position of the fluorophores 1-bromo-4-oxo-4H-quinolizine-3-carboxylic acid (9a) and 1-bromo-8-(1,2-dicarboxyethyl)-4-oxo-4H-quinolizine-3-carboxylic acid (21a) resulted in a bathochromic shift of 18 nm and 26 nm, respectively, when binding $Mg^{2+}$. These fluorophores display well-separated fluorescence maxima for the free and magnesium-bound state, with crossover points at 446 nm (FIG. 13) and 451 nm (FIG. 14), respectively. Both fluorophores show no fluorescent response to increasing $Ca^{2+}$ concentrations up to 100 mM, as exemplified for (21a) in FIG. 15. In addition, the carboxylate group on the ring system of (21a), which is believed to be involved in forming the metal ion-complex was determined to have a $pK_a$ of 5.6 by a fluorescence/pH titration. However, it is not intended that the present invention be so limited nor is it necessary to understand the mechanism in order to practice the present invention. Thus, the indicators are present in the deprotonated form and available for complexation at physiological pH.

However, alkylation at the 8-position such as in 8-(carboxymethyl)-4-oxo-4H-quinolizine-3-carboxylic acid (19a) and 8-(1,2-dicarboxyethyl)-4-oxo-4H-quinolizine-3-carboxylic acid (20a), results in overlap of the fluorescence spectra. Although it is not necessary to understand the mechanism in order to practice the present invention, nor is it intended that the present invention be so limited, the introduction of a substituent that can perturb the π-system of the 4-oxo-4H-quinolizine 3-carboxylic acid fluorophore is believed to diminish the degree of emission shift of the fluorophore.

Figure 16:
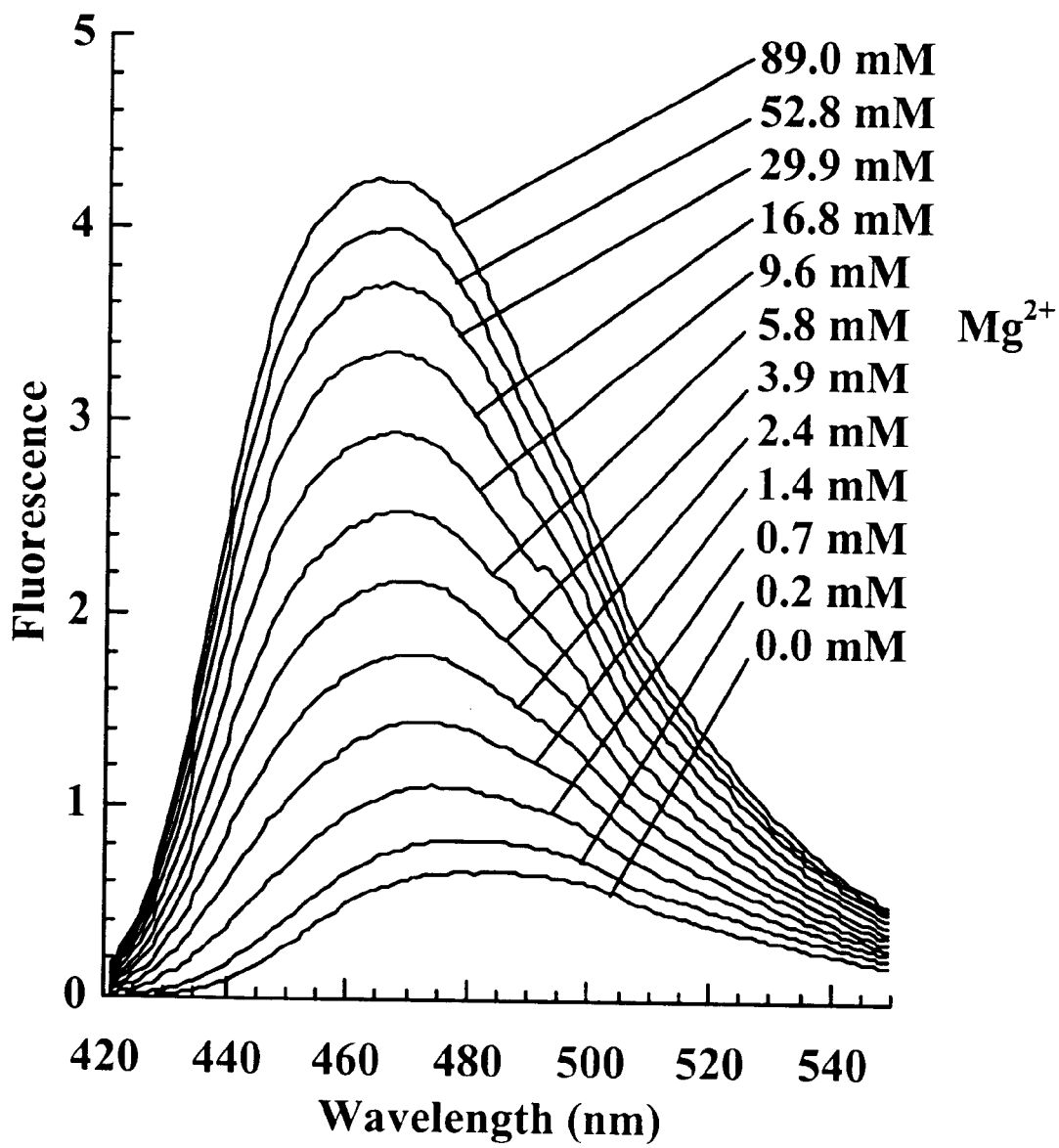
FIG. 16 shows the fluorescence emission of [6,7]-benzo-4-oxo-4H-quinolizine-3-carboxylic acid (3a), upon complexation with $Mg^{2+}$.
Figure 17:
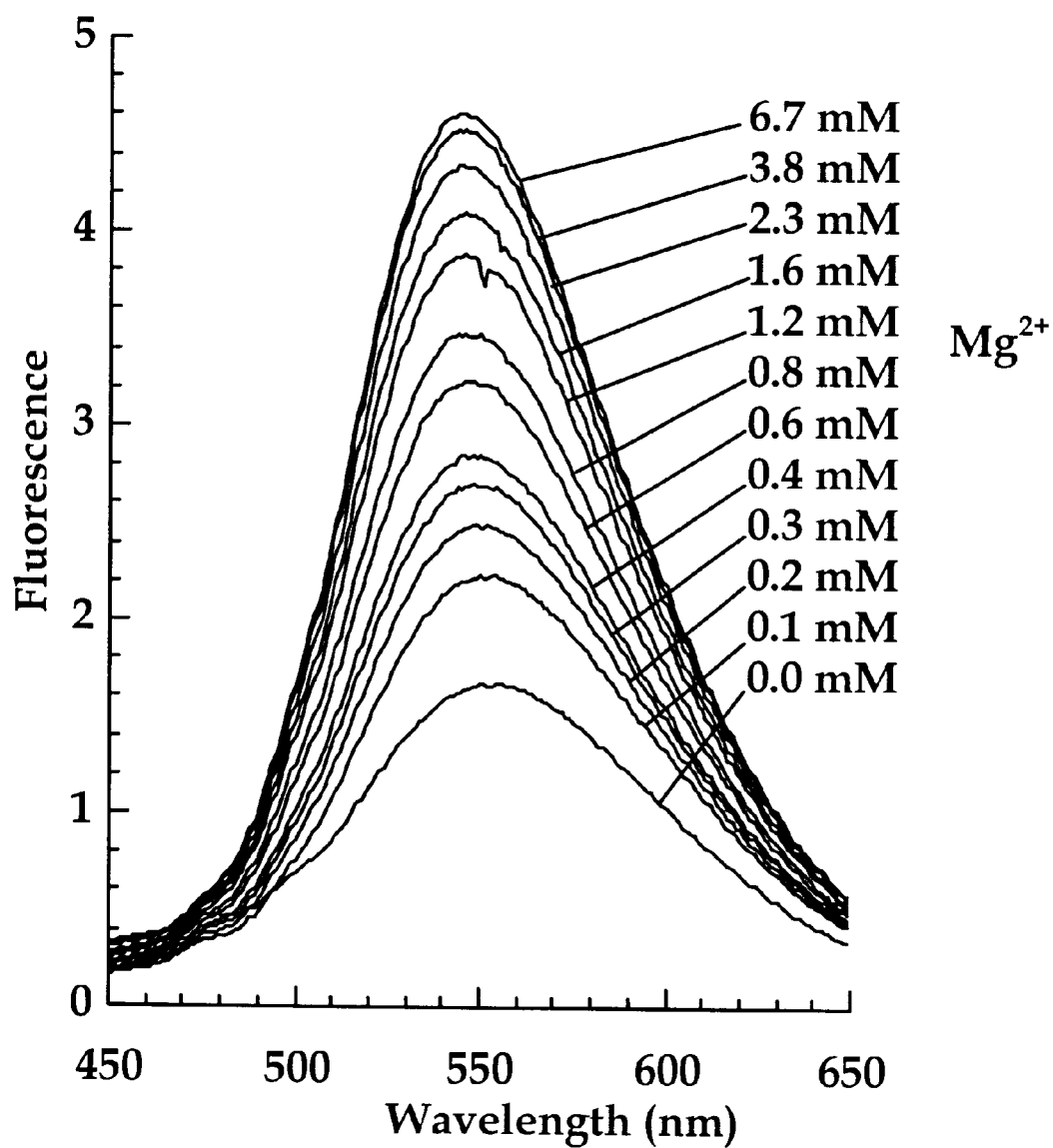
FIG. 17 shows the fluorescence emission of 1-[N,N-di(carboxymethyl)]-4-oxo-4-H-quinolizine-3-carboxylic acid (i.e., compound 11a), upon complexation with $Mg^{2+}$.

Fluorophores [6,7]-benzo-4-oxo-4H-quinolizine-3-carboxylic acid (3a) (FIG. 16), 1-[N,N-di(carboxymethyl)]-4-oxo-4H-quinolizine-3-carboxylic acid (11a) (FIG. 17), 8-(naphth-1-yl)-4-oxo-4H-quinolizine-3-carboxylic acid (23a) and 8-(benzo[b]furyl)-4-oxo-4H-quinolizine-3-carboxylic acid (24a), show an increase of the fluorescence emission when binding to $Mg^{2+}$, and are sensitive to changing $Mg^{2+}$ levels. The triacid 1-[N,N-di(carboxymethyl)]-4-oxo-4H-quinolizine-3-carboxylic acid (11a) exhibits a fluorescence maximum at 552 nm, making this compound an attractive fluorescent magnesium indicator. The presence of the amino group at the 1-position gave a hypsochromic shift of 117 nm with respect to 4-oxo-4H-quinolizine-3-carboxylic acid (1a). The introduction of an aromatic moiety at the 8-position (e.g., 8-(4-methoxyphenyl)-4-oxo-4H-quinolizine-3-carboxylic acid [22a]; 8-(naphth-1-yl)-4-oxo-4H-quinolizine-3-carboxylic acid [23a]; and 8-(benzo[b]furyl)-4-oxo-4H-quinolizine-3-carboxylic acid [24a]), or extension of the 7-system as in [6,7]-benzo-4-oxo-4H-quinolizine-3-carboxylic acid (3a) are believed to result in a hypsochromic shift to longer wavelengths, although it is not necessary to understand the mechanism in order to practice the present invention and it is not intended that the present invention be so limited. However, the hypsochromic shifts of these compounds are smaller in comparison to the hypsochromic shift exhibited by 1-[N,N-di(carboxymethyl)]-4-oxo-4H-quinolizine-3-carboxylic acid (11a).

In sum, 4-oxo-4H-quinolizine-3-carboxylic acids are a new class of $Mg^{2+}$-selective, fluorescent indicators. The dissociation constants ($K_d$) for the 4-oxo-4H-quinolizine-3-carboxylic acid derivatives of the present invention range from 0.4 mM for 1-[N,N-di(carboxymethyl)]-4-oxo-4H-quinolizine-3-carboxylic acid (11a) and 8-(1,2-dicarboxyethyl)-4-oxo-4H-quinolizine-3-carboxylic acid (20a) to 5.0 mM for 4-oxo-8-chloro-4H-quinolizine-3-carboxylic acid (2a), corresponding well with commonly observed intracellular $Mg^{2+}$ levels, a requirement for optimal sensitivity, in particularly preferred embodiments. The fluorophores showed very little, if any change of the fluorescence emission in the presence of $Ca^{2+}$. The observed changes of the fluorescence emission with increasing $Mg^{2+}$ levels were found to depend upon the substitution pattern of the 4-oxo-4H-quinolizine-3-carboxylic acid.

Figure 18:
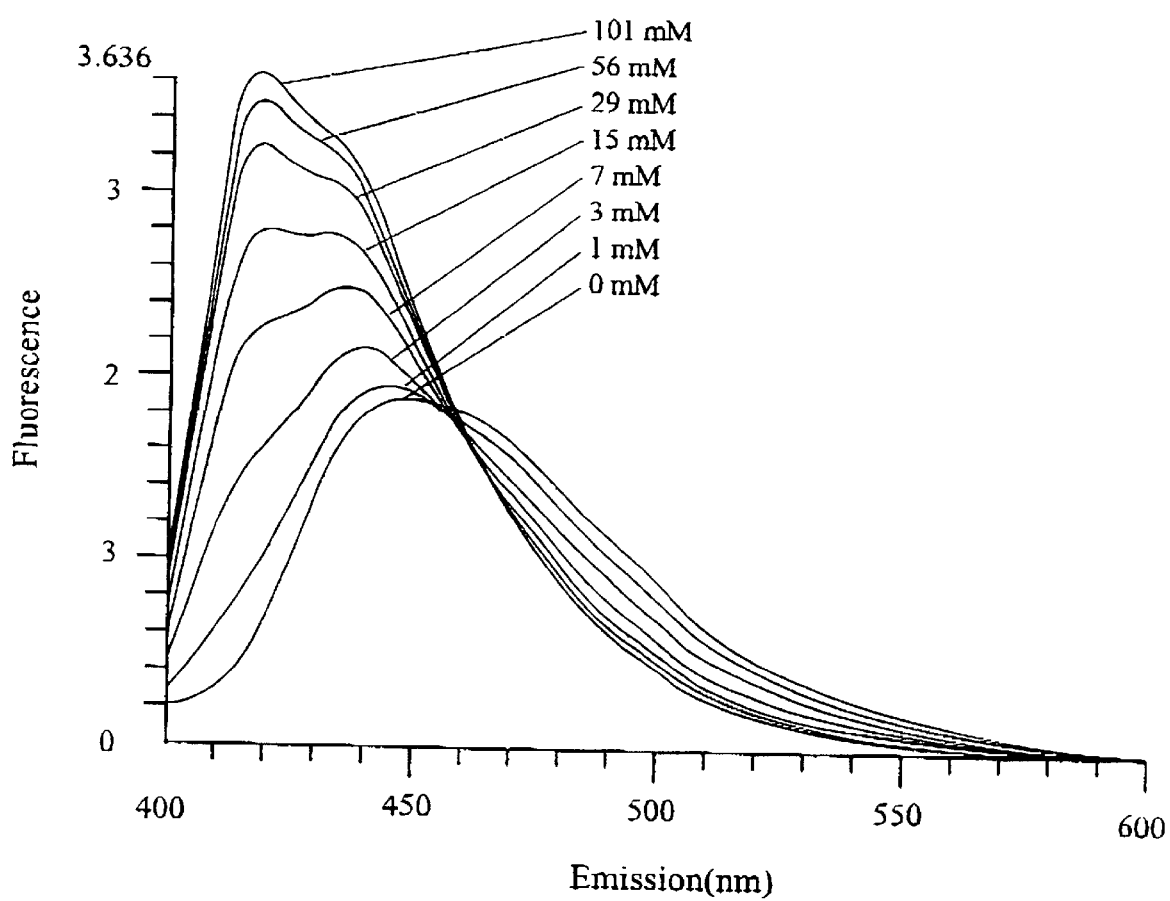
FIG. 18 shows the fluorescence emission spectrum of 4-oxo-8-chloro-4H-quinolizine-3-carboxylic acid (2a), upon complexation with $Mg^{2+}$.
Figure 19:
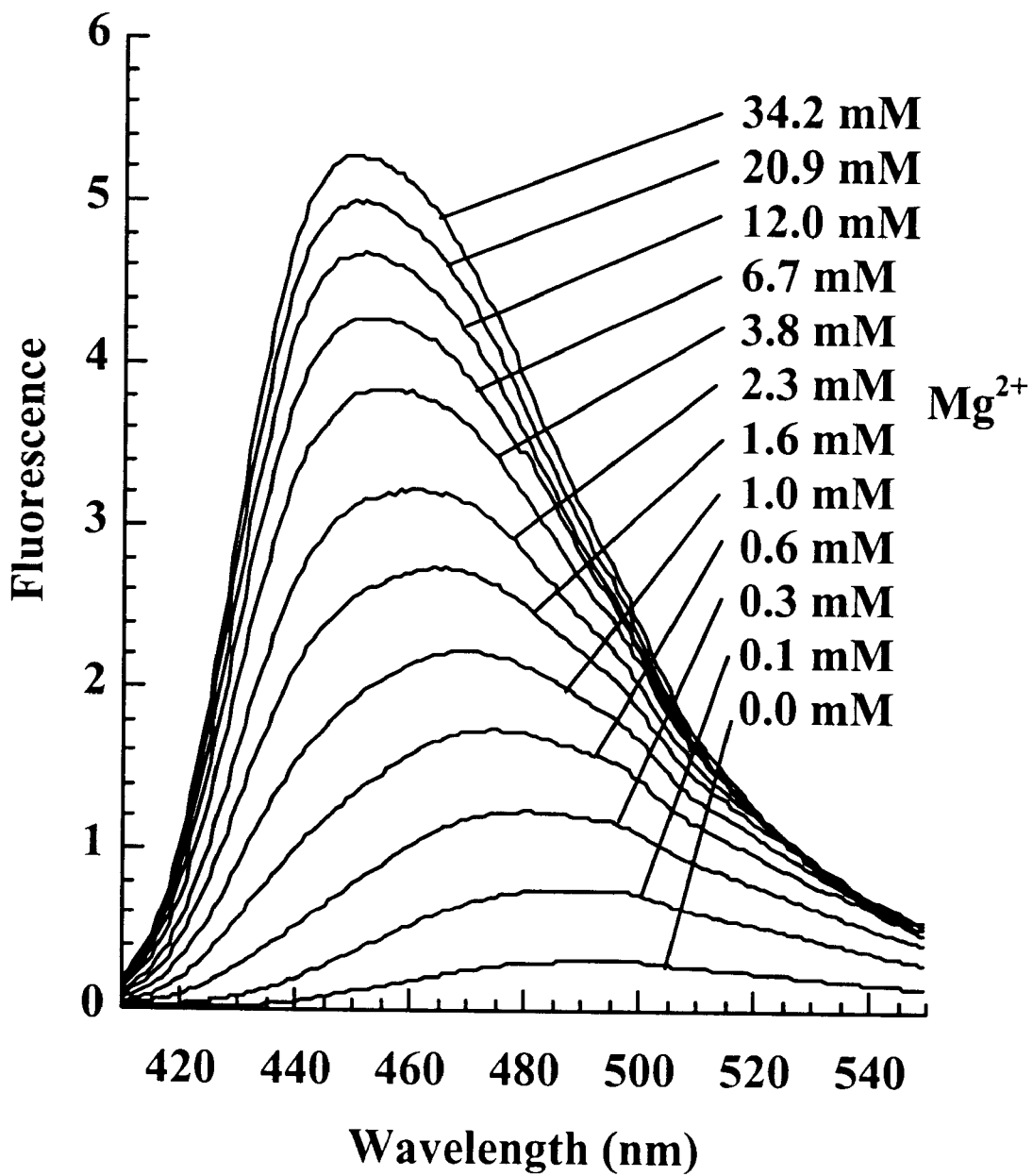
FIG. 19 shows the fluorescence emission spectrum of 8-(naphth-1-yl)-4-oxo-4H-quinolizine-3-carboxylic acid (23a), upon complexation with $Mg^{2+}$.
Figure 20:
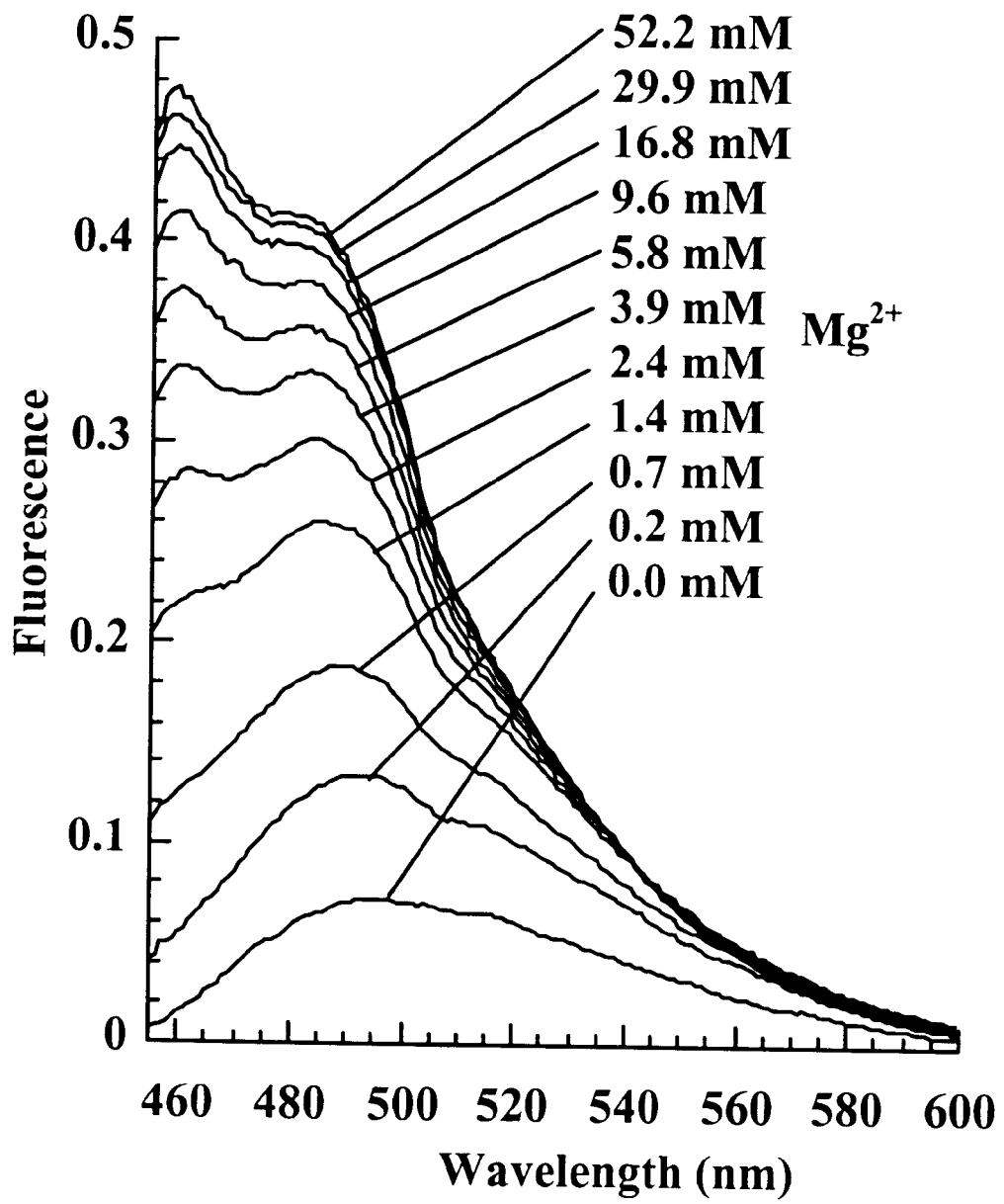
FIG. 20 shows the fluorescence emission spectrum of 8-(benzo[b]furyl)-4-oxo-quinolizine-3-carboxylic acid (24a), upon complexation with $Mg^{2+}$.

Although it is not necessary to understand the mechanism in order to practice the present invention nor is it intended that the present invention be so limited, the presence of two additional carboxylates in the fluorophores is believed to decrease the dissociation constants through electrostatic interactions. The lowering effect on the dissociation constants can also be seen when comparing the dissociation constants for 1-bromo-4-oxo-4H-quinolizine-3-carboxylic acid (9a) at 1.5 mM, and for 1-bromo-8-(1,2-dicarboxyethyl)-4-oxo-4H-quinolizine-3-carboxylic acid (21a) at 0.7 mM, which contains two extra carboxylates. The electron-withdrawing nature of the chloro substituent at the 8-position of 4-oxo-8-chloro-4H-quinolizine-3-carboxylic acid (2a) results in a weaker complex with $Mg^{2+}$ (FIG. 18), as shown by its higher dissociation constant at 5 mM compared to 1.1 mM for 4-oxo-4H-quinolizine-3-carboxylic acid (1a). Stearic interaction between the extended and angled aromatic system of [6,7]-benzo-4-oxo-4H-quinolizine-3-carboxylic acid (3a) and additional complexing ions or water molecules around the $Mg^{2+}$ ion might account for the higher dissociation constant of 4.6 mM of this compound, although it is not necessary to understand the mechanism in order to practice the present invention nor is it intended that the present invention be so limited.

III. Use of 4-oxo-4H-Quinolizine-3-carboxylic Acid Derivatives

In some experiments a test carboxy-quinolizine compound was loaded into Sup+ cells (i.e., a variant of Syrian Hamster embryo cells) via a "scrape loading" procedure (McNeil et al., J. Cell Biol. 98: 1556–1564 [1984]). Using this indicator, a value of $[Mg^{2+}]=1.10\pm0.12$ mM in controls, and a value of $[Mg^{2+}]=0.53\pm0.03$ mM in cells induced to undergo apoptosis by exposure to low serum levels were obtained. This significant reduction of $[Mg^{2+}]$ observed in the apoptotic cells was unexpected. Thus, 4-oxo-4H-quinolizine-3-carboxylic acids are excellent fluorophores that respond to changing $Mg^{2+}$ levels. The dissociation constants for $Mg^{2+}$ were found in the low or submillimolar range, at approximately 1 mM. In addition, these fluorophores either do not respond, or minimally respond to $Ca^{2+}$ well above basal intracellular levels. These fluorophores are the first fluorescent indicators that exhibit such selectivity for $Mg^{2+}$.

In addition to the above methods, the compounds of the present invention find use in conjunction with the commonly used and known assay method to detect ions in cells and in biological fluids. Indeed, the compounds of the present invention find use in the selective detection of magnesium (e.g., $Mg^{2+}$) within cells (i.e., intracellularly), as well as in acellular fluids (e.g., serum). As polycarboxylate indicators can be loaded into cells via use of the acetoxymethyl ester (See, Tsien, Nature 290:527–528 [1981]), the compounds of the present invention find use with various assay systems known in the art. For example, the methods described Grynkiewicz et al. (Grynkiewicz et al., J. Biol. Chem. 260: 3440–3450 [1985]) are suitable for use with the present invention. Additional assay systems suitable for use with the present invention include long-known and well-described methods (See e.g., Tsien, Ann. Rev. Biophys. Bioeng., 12:94–116 [1983]; Tsien, Ann. Rev. Neurosci., 12:227–253 [1989]; and Tsien and Poenie, Trends Biochem. Sci., 11:450–455 [1986]). As the compounds of the present invention find use in various assay systems, it is not intended that the present invention be limited to any particular assay method or system to detect magnesium (e.g., $Mg^{2+}$) in samples.

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); mM (millimolar); μM (micromolar); N (Normal); mol (moles); mmol (millimoles); μmol (micromoles); g (grams); mg (milligrams); μg (micrograms); l or L (liters); ml or mL (milliliters); μL (microliters); ° C. (degrees Centigrade); min (minute or minutes); h (hour or hours); m.p. (melting point); NMR (nuclear magnetic resonance); TLC (thin layer chromatography); UV (ultraviolet); $^1$H NMR (proton nuclear magnetic resonance spectroscopy); $^{13}$C NMR (carbon-13 nuclear magnetic resonance spectroscopy); Hz (hertz); J (coupling constant); d (doublet); dd (doublet of doublets); s (singlet); br s (broad singlet); t (triplet); m (multiplet); δ (nuclear magnetic resonance chemical shift); $D_2O$ (deuterated water); $NaCNBH_3$ (sodium cyanoborohydride); NaI (sodium iodide); LDA (lithium diisopropylamide); $HNO_3$ (nitric acid); HCl (hydrochloric acid); DMF (dimethylformamide); THF (tetrahydrofuran); NaOH (sodium hydroxide); H (hydrogen); Li (lithium); C (carbon); N (nitrogen); O (oxygen); Cl (chlorine); Br (bromine); Pd (palladium); $NaN_3$ (sodium azide); NaH (sodium hydride); DMSO (dimethylsulfoxide); $Br_2$ (bromine); n-BuLi (n-butyl lithium); $CDCl_3$ (deuterated chloroform); $CHCl_3$ (chloroform); DMSO-$d_6$ (deuterated dimethylsulfoxide); EtOAc (ethyl acetate); AcOH (acetic acid); $CH_2Cl_2$ (dichloromethane); $Et_2O$ (diethyl ether); $PdCl_2[P(c-Hex)_3]_2$ (dichlorobis[trichlorohexylphosphine) palladium(II)]; NaOD (sodium deuteroxide); $CO_2$ (carbon dioxide); KCl (potassium chloride); NaCl (sodium chloride); $MgCl_2$ (magnesium chloride); EMME (diethyl ethoxymethylene malonate); $POCl_3$ (phosphorus oxychloride); $Ac_2O$ (acetic anhydride); $NH_4OAc$ (ammonium acetate); $CH_2(CO_2Et)_2$ (diethyl malonate); MeCN (acetonitrile); and $BrCH_2CO_2Me$ (methyl bromoacetate). PROTON SPONGE® is 1,8-(bis-(dimethylamino)-naphthalene (or N,N,N',N'-tetramethyl-1, 8-naphthalenediamine), sold by Sigma-Aldrich (Sigma-Aldrich, St. Louis, Mo.). In some experiments, pH 2 HYDRION® buffer (Sigma-Aldrich) was used to adjust the pH of solutions.

In the following experiments, tetrahydrofuran (THF) was dried and distilled over sodium/benzophenone (Nalbenzophenone) prior to use. Dimethylformamide (DMF) was dried over molecular sieves (4 Å). Ethyl acetate, hexane, diethyl ether and all commercially available chemicals were used as received. After extractive work-up, the combined organic phases were dried on magnesium sulfate. Water used in the spectrophotometric and fluorescence experiments was filtered through a hydro PICOPURE® 2 filter. Thin layer chromatography was carried out on Sigma-Aldrich TLC plates (silica gel on polyester). Chromatographic purifications were done by flash chromatography using Merck Silica Gel, grade 9385, 230–400 mesh, 60 Å. Melting points were measured on a Fisher-Johns melting point apparatus and are shown uncorrected herein. $^1$H-NMR spectra and $^{13}$C-NMR spectra were recorded on a Nicolet NT 360 MHz NMR Spectrometer and a Varian UNITY plus 400 MHz NMR Spectrometer. Chemical shifts are reported in parts per million (δ), using tetramethylsilane (TMS) as the internal standard. The signals are expressed as an s (singlet), d (doublet), t (triplet), q (quartet), m (multiplet), or br (broad). High cresolution mass spectra were obtained from the Washington University Resources for Biomedical and Bio-organic Mass Spectrometry on samples which were chromatographically pure. Compounds (9a) and (21a) were analyzed by FABMS using NBA Li matrix. UV absorption spectra were recorded with a Bechman DU 650 Spectrophotometer using Fisherbrand™ semimicro quartz cells (Fisher Scientific). Fluorescence measurements were recorded with an Aminco-Bowman® Series 2 Spectrometer using quartz fluorimeter cuvets from Sigma. pH measurements were done using a Mettler Toledo MP 255 pH meter.

The buffered solutions used in fluorescence/$Mg^{2+}$ titration experiments contained 120 mM KCl, 20 mM NaCl, and 15 mM TRIS buffer, and were brought to pH=7.2 with concentrated HCl. A stock solution of 2 mg of the indicator in 5 ml buffer was prepared. To record a UV spectrum, the stock solutions were diluted 40 times (25 μl in 975 μl). For the fluorescence titration experiments, 25 μl of the stock solution was diluted 100 times with 2475 μl buffer. Emission fluorescence and excitation fluorescence spectra were recorded using the appropriate excitation wavelength derived from the UV spectrum of the free indicator. To 2475 μl of a $MgCl_2$ solution (100 mM, 250 mM or 500 mM (2a)), 25 μl of the stock solution of the indicator was added, to cancel out dilution during the titration. To the solution of the free indicator, increasing amounts of the $MgCl_2$/indicator solution were added. After each titration step, fluorescence emission and fluorescence excitation spectra were recorded.

To determine the pKa of 1-bromo-8-(1,2-dicarboxyethyl)-4-oxo-4H-quinolizine-3-carboxylic acid (21a), 250 μl of the stock solution of 1-bromo-8-(1,2-dicarboxyethyl)-4-oxo-4H-quinolizine-3-carboxylic acid was added to 25 ml of 10 mM MOPS, pH 4.29. The fluorescence emission spectrum was recorded. A 0.1 M NaOH solution containing an equal concentration of 1-bromo-8-(1,2-dicarboxyethyl)-4-oxo-4H-quinolizine-3-carboxylic acid (21a), was added dropwise. After each pH increase of 0.2, the emission spectrum was recorded. At pH 6.31, no change of the fluorescence emission was observed. The fluorescence emission was plotted against the pH to determine pKa, which was found to be 5.6.

EXAMPLE 1

Preparation of Ethyl 8-Chloro-4-oxo-4H-quinolizine-3-carboxylate (2)

A 250 mL oven-dried (140° C.), three-necked, round-bottom flask, equipped with an oven-dried 100 mL addition funnel and a pentane thermometer was purged with argon. The flask was charged with 50 ml dry THF and duisopropylamine (7.2 mL, 50 mmol, dried over NaOH). The addition funnel was charged with a solution of 4-chloro-2-picoline (5.0 g, 40 mmol) in 50 ml dry THF. The mixture was cooled to −50° C., and 20 mL of a 1.6 M solution of n-BuLi in hexanes was added rapidly through a syringe. Stirring was continued for 30 min. The reaction mixture was cooled to −78° C., and the picoline solution was added over a 15 min period, while the temperature of the reaction mixture was maintained below −60° C. The reaction mixture was stirred for 30 min during which a bright red suspension formed. The addition funnel was charged with a solution of diethyl ethoxymethylenemalonate (9.5 g, 45 mmol) in 25 ml of dry THF, and the solution was added slowly to the reaction mixture, while maintaining the temperature below −60° C. A clear, pale yellow solution formed and the reaction mixture was warmed to −20° C. over a period of 2 h. The reaction mixture was subsequently poured into 500 ml water and extracted three times with 300 ml of dichloromethane ($CH_2Cl_2$). Subsequent evaporation of the organic solvent gave a yellow oil (13.30 g, 96%), which was dissolved in 60 mL of xylene. The reaction mixture was refluxed for 16 h, cooled to room temperature and filtered to give an orange crystalline residue. The xylene in the filtrate was evaporated in vacuo, and the remaining orange solid was stirred overnight with 30 ml ether ($Et_2O$) and filtered. The combined filtration residues were dried in vacuo on KOH to give ethyl 8-chloro-4-oxo-4H-quinolizine-3-carboxylate (6.28 g, 63%). M.p. 161–164° C. $^1$H NMR (δ, $CDCl_3$): 1.42 (t, J=7 Hz, 3H), 4.41 (q, J=7 Hz, 2H), 6.55 (d, J=8 Hz, 1H), 7.09 (dd, J=2 Hz, J=7 Hz, 1H), 7.53 (d, J=2 Hz, 1H), 8.40 (d, J=8 Hz, 1H), 9.29 (d, J=7 Hz, 1H). MS: m/z 251.0360; required for $C_{12}H_{10}ClNO_3$: 251.0349.

EXAMPLE 2

Preparation of Ethyl 4-oxo-4H-quinolizine-3-carboxylate (1)

Using the procedure described in Example 1, ethyl 4-oxo-4H-quinolizine-3-carboxylate (1) was obtained as an orange crystalline material in 55% yield, after purification by flash chromatography (EtOAc). M.p. 105–109° C. $^1$H NMR (δ, $CDCl_3$): 1.43 (t, J=7.0 Hz, 3H), 4.42 (q, J=7.0 Hz, 2H), 6.65 (d, J=8.4 Hz, 1H), 7.16–7.24 (m, 1H), 7.52–7.66 (m, 2H), 8.41 (d, J=8.4 Hz, 1H), 9.40 (d, J=7.3 Hz, 1H). MS: (m/z) 217.0735; required for $C_{12}H_{11}NO_3$: 217.0738.

EXAMPLE 3

Preparation of Ethyl Benzo[6,7]-4-oxo-4H-quinolizine-3-carboxylate (3)

Using the procedure described in Example 1, ethyl benzo[6,7]-4-oxo-4H-quinolizine-3-carboxylate (3) was obtained as an orange powder in 45% yield, after purification by flash chromatography (7:3 ethyl acetate/hexane). M.p. 106–108° C. $^1$H NMR (δ, $CDCl_3$): 1.42 (t, J=7.0 Hz, 3H), 4.42 (q, J=7.0 Hz, 2H), 6.49 (d, J=9.7 Hz, 1H), 7.14 (d, J=9.2 Hz, 1H), 7.48–7.64 (m, 4H), 8.27 (d, J=7.7 Hz, 1H), 9.87 (d, J=8.8 Hz, 1H). MS: m/z 267.0908; required for $C_{16}H_{13}NO_3$: 267.0895.

EXAMPLE 4

Preparation of Ethyl 1-nitro-4-oxo-4H-quinolizine-3-carboxylate (7)

Nitric acid (1.08 g, 17 mmol) was added slowly to acetic anhydride (7 mL) at 5° C. Stirring was continued for 5 min and the reaction mixture was cooled to −10° C. (ice/salt bath). Ethyl 4-oxo-4H-quinolizine-3-carboxylate (1) (920 mg, 4.2 mmol) was added in one portion. After 5 min, an orange precipitate formed. The reaction was complete after 15 min as indicated by thin layer chromatography (ethyl acetate). The reaction mixture was poured into 250 g crushed ice and stirred for 30 min to give an orange suspension, which was extracted three times with 100 mL dichloromethane. The combined organic layers were washed three times with 100 ml water. Evaporation of the solvent gave a deep red solid. Purification by flash chromatography gave a bright yellow solid (497 mg, 50% yield). M.p. 169–170° C. $^1$H NMR (δ, $CDCl_3$): 1.44 (t, J=7.0 Hz, 3H), 4.45 (q, J=7.0 Hz, 2H), 7.55 (dd, J=7.0 Hz, J=7.0 Hz, 1H), 8.15 (dd, J=9.7 Hz, 7.0 Hz, 1H), 9.31 (d, J=9.1 Hz, 1H), 9.47 (s, 1H), 9.60 (d, J=7.0 Hz, 1H). MS: m/z 262.0601; required for $C_{12}H_{10}N_2O_5$: 262.0590.

EXAMPLE 5

Preparation of Ethyl 1-[N,N-di(Carbomethoxymethyl)]-4-oxo-4H-quinolizine-3-carboxylate (11)

A suspension of ethyl 1-nitro-4-oxo-4H-quinolizine-3-carboxylate (7) (540 mg, 2.0 mmol) and 5% Pd on carbon in 25 ml ethanol was stirred under ambient hydrogen pressure until 50 ml of hydrogen was absorbed by the reaction mixture. Complete reaction of the starting material was confirmed by thin layer chromatography (ethyl acetate). The reaction mixture was filtered and the solvent was evaporated in vacuo, which gave a red solid (400 mg, 86% yield). The crude product was dissolved in 9 ml dry acetonitrile, followed by addition of methyl bromoacetate (1.0 ml, 11 mmol), NaI (1.5 g, 10 mmol), and PROTON SPONGES® (2.6 g, 12 mmol). The reaction mixture was refluxed for 17 h, cooled to room temperature and poured into 200 ml ethyl acetate. The resulting suspension was stirred for 1 h, filtered, and the red filtrate was washed three times with a buffer solution (pH 2), until an acid reaction was indicated on litmus paper. The solvent was evaporated and the crude product was purified by flash chromatography to give a yellow solid (410 mg, 54% yield). M.p. 145–148° C. $^1$H NMR ($\delta$, CDCl$_3$): 1.43 (t, J=7 Hz, 3H), 3.88 (s, 6H), 4.08 (s, 4H), 4.42 (q, J=7 Hz, 4H), 7.23 (dd, J=7 Hz, J=7 Hz, 1H), 7.72 (dd, J=7 Hz, J=7 Hz, 1H), 8.50 (d, J=8 Hz, 1H), 8.62 (s, 1H), 9.43 (d, J=7 Hz). MS: m/z 376.1252; required for $C_{18}H_{20}N_2O_7$: 376.1270.

EXAMPLE 6

Preparation of Ethyl 1-Formyl-4-oxo-4H-quinolizine-3-carboxylate (8)

Ethyl 4-oxo-4H-quinolizine-3-carboxylate (1) (1 g, 4.0 mmol) was dissolved in 2 ml DMF followed by the addition of POCl$_3$ (1.0 ml, 11 mmol). The reaction mixture was stirred for 1 h, poured into 100 ml water and extracted three times with 100 ml dichloromethane. Evaporation of the organic solvent gave a sticky yellow solid, which was further purified by flash chromatography (ethyl acetate), followed by overnight stirring with 10 ml ether to remove the last traces of DMF. Filtration of the suspension and drying in vacuo gave a bright yellow powder (920 mg, 93%). M.p. 179–181° C. $^1$H NMR ($\delta$, CDCl$_3$): 1.43 (t, J=7 Hz), 4.42 (q, J=7 Hz), 7.51 (dd, J=7 Hz, J=7 Hz, 1H), 8.06 (dd, J=7, J=7 Hz, 1H), 8.80 (s, 1H), 9.57 (d, J=7 Hz), 9.90 (s, 1H). MS: m/z 245.0683; required for $C_{13}H_{11}NO_4$: 245.0688.

EXAMPLE 7

Preparation of Ethyl 1-Bromo-4-oxo-4H-quinolizine-3-carboxylate (9)

To a solution of ethyl 4-oxo-4H-quinolizine-3-carboxylate (1) (2.33 g, 10.7 mmol) in 20 ml acetic acid was rapidly added a solution of bromine (1.9 g, 12 mmol) in 10 ml acetic acid. The reaction was complete after 5 min, as indicated by thin layer chromatography (ethyl acetate). The solvent was evaporated in vacuo and the remaining yellow solid was dissolved in 20 ml dichloromethane. To this solution, silica gel (3 g) was added and the solvent was evaporated in vacuo. The silica gel was poured on a pre-packed column and eluted with ethyl acetate to give ethyl 1-bromo-4-oxo-4H-quinolizine-3-carboxylate (9) as a bright yellow solid (2.1 g, 71%). M.p. 156–158° C. $^1$H NMR ($\delta$, CDCl$_3$): 1.43 (t, J=7 Hz, 3H), 4.43 (q, J=7 Hz, 2H), 7.03 (dd, J=7 Hz, J=7 Hz, 1H), 7.30 (dd, J=7 Hz, 2H), 7.80 (dd, J=7 Hz, J=7 Hz, 1H), 8.63 (s, 1H), 9.49 (d, J=7 Hz). MS: m/z 294.9839; required for $C_{12}H_{10}BrNO_3$: 294.9843.

EXAMPLE 8

Preparation of Ethyl 1-(2,2-Dicarboethoxyvinyl)-4-oxo-4H-quinolizine-3-carboxylate (12)

A 100 ml round-bottom flask equipped with a Dean-Stark trap was charged with 50 ml benzene, ethyl 1-formyl-4-oxo-4H-quinolizine-3-carboxylate (8) (1.22 g, 5 mmol), acetic acid (5 g, 83 mmol), NH$_4$OAc (5 g, 65 mmol), and diethyl malonate (2.3 g, 9 mmol). The reaction mixture was refluxed for 48 h. The reaction mixture was cooled to room temperature and washed three times with 50 ml water. The solvent was evaporated in vacuo and the crude product was purified by flash chromatography (ethyl acetate) to yield ethyl 1-(2,2-dicarboethoxyvinyl)-4-oxo-4H-quinolizine-3-carboxylate (12) as a yellow powder (1.58 g, 82%). M.p. 149–151° C. $^1$H NMR ($\delta$, CDCl$_3$): 1.31 (t, J=7 Hz, 3H), 1.36 (t, J=7 Hz, 3H), 1.42 (t, J=7 Hz, 3H), 4.34 (q, J=7 Hz, 2H), 4.36 (q, J=7 Hz, 2H), 4.41 (q, J=7 Hz, 2H), 7.34 (dd, J=7 Hz, J=7 Hz, 1H), 7.82 (dd, J=8 Hz, 1H), 7.96 (d, J=8 Hz, 1H), 8.05 (s, 1H), 8.60 (s, 1H), 9.50 (d, J=7 Hz). MS: m/z 387.1331; required for $C_{20}H_{21}NO_7$: 387.1318.

EXAMPLE 9

Preparation of Ethyl 1-(2,2-Dicarboethoxyethyl)-4-oxo-4H-quinolizine-3-carboxylate (13)

To a bright yellow suspension of ethyl 1-(2,2-dicarboethoxyvinyl)-4-oxo-4H-quinolizine-3-carboxylate (12) (750 mg, 1.94 mmol) in 5 ml ethanol was added NaBH$_3$CN (68 mg, 1.08 mmol). The reaction mixture turned red and all solid material dissolved. Stirring was continued for 1 h, and the reaction mixture was poured into 50 ml of water. Ethanol was added to the aqueous suspension until a clear solution was obtained, which was extracted three times with 100 ml dichloromethane. The organic solvent was evaporated and the crude product was purified by flash chromatography to give ethyl 1-(2,2-dicarboethoxyethyl)-4-oxo-4H-quinolizine-3-carboxylate (13) as a bright yellow solid (275 mg, 36%). M.p. 105–108° C. $^1$H NMR ($\delta$, CDCl$_3$): 1.22 (t, J=7 Hz, 6H), 1.41 (t, J=7 Hz, 3H), 3.41 (d, J=7 Hz, 2H), 3.65 (t, J=7 Hz, 1H), 4.10–4.25 (m, 4H), 4.41 (q, J=7 Hz, 2H), 7.23 (m, 1H), 7.70 (m, 1H), 7.84 (d, J=8 Hz, 1H), 8.33 (s, 1H), 9.50 (d, J=7 Hz, 1H). MS: m/z 389.1466; required for $C_{20}H_{23}NO_7$: 389.1475.

EXAMPLE 10

Preparation of Ethyl 8-Azido-4-oxo-4H-quinolizine-3-carboxylate (14)

An oven-dried 25 ml round-bottom flask was purged with argon and charged with ethyl 8-chloro-4-oxo-4H-quinolizine-3-carboxylate (2) (250 mg, 1 mmol), NaN$_3$ (300 mg, 4.6 mmol), and 5 ml DMF. The reaction mixture was stirred at 40° C. for 1 h, cooled to room temperature, and poured into 100 ml water. The aqueous layer was extracted three times with 100 ml chloroform, and the combined organic layers were washed three times with 100 ml water. The organic solvent was evaporated and the crude product was purified by flash chromatography (ethyl acetate) to give a deep red crystalline solid (218 mg, 85%). M.p. 145–150° C. $^1$H NMR ($\delta$, CDCl$_3$): 1.42 (t, J=7 Hz, 3H), 4.41 (q, J=7 Hz, 2H), 6.53 (d, J=8 Hz, 1H), 6.84 (dd, J=2 Hz, J=7 Hz, 1H), 7.08 (d, J=2 Hz, 1H), 8.37 (d, J=8 Hz, 1H), 9.36 (d, J=7 Hz, 1H). MS: m/z 258.0751; required for $C_{12}H_{10}N_4O_3$: 258.0753.

EXAMPLE 11

Preparation of Ethyl 8-Amino-4-oxo-4H-quinolizine-3-carboxylate (15)

A suspension of ethyl 8-azido-4-oxo-4H-quinolizine-3-carboxylate (14) (253 mg, 1.0 mmol) and 20 mg 5% Pd on carbon in 15 ml ethanol was stirred under ambient hydrogen pressure. The color of the reaction mixture rapidly changed from deep red to dark yellow. After 30 ml of hydrogen was absorbed by the reaction mixture, the catalyst was filtered off and the solvent was evaporated to give ethyl 8-amino-4-oxo-4H-quinolizine-3-carboxylate (15) (221 mg, 94%) as a yellow green powder. M.p.>250° C. $^1$H NMR ($\delta$, DMSO-$d_6$): 1.23 (t, J=7 Hz, 3H), 4.13 (q, J=7 Hz, 2H), 6.23 (d, J=7 Hz, 1H), 6.53 (d, J=2 Hz, 1H), 6.79 (dd, J=2 Hz, J=7 Hz, 1H), 7.32 (s, 2H), 7.81 (d, J=8 Hz, 1H), 8.94 (d, J=7 Hz, 1H). MS: m/s 232.0837; required for $C_{12}H_{12}NO_3$: 232.0848.

EXAMPLE 12

Preparation of Ethyl 8-(3-Nitrophenoxy)-4-oxo-4H-quinolizine-3-carboxylate (16)

An oven-dried 50 ml three-necked round-bottom flask was purged with argon and charged with sodium hydride (200 mg, 60% suspension in oil, 5 mmol and washed with hexane) and 10 ml dry DMF. To this suspension, m-nitrophenol (626 mg, 4.5 mmol) was added in one portion. After gas evolution had ceased, ethyl 8-chloro-4-oxo-4H-quinolizine-3-carboxylate (2) (1.00 g, 4 mmol) was added in one portion and stirring was continued at room temperature for 2 h. When the reaction was complete as indicated by thin layer chromatography (ethyl acetate), the reaction mixture was poured into 250 ml of water. The aqueous layer was extracted three times with 200 ml dichloromethane, and the combined organic layers were washed three times with 200 ml water. The organic solvent was evaporated and the crude product was stirred overnight with 30 ml ether. Filtration gave a bright yellow solid (950 mg, 67%). M.p. 161–163° C. $^1$H NMR ($\delta$, CDCl$_3$): 1.42 (t, J=7 Hz, 3H), 4.41 (q, J=7 Hz, 2H), 6.39 (d, J=8 Hz, 1H), 6.70 (d, J=2 Hz, 1H), 6.99 (dd, J=0.5 Hz, J=7 Hz, 1H), 7.55 (d, J=7 Hz, 1H), 7.72 (dd, J=8 Hz, J=8 Hz, 1H), 8.07 (s, 1H), 8.24 (d, J=8 Hz, 1H), 8.32 (d, J=8 Hz, 1H), 9.43 (d, J=7 Hz, 1H). MS: m/z 354.0850; required for $C_{18}H_{14}N_2O_6$: 354.0852.

EXAMPLE 13

Preparation of Ethyl 8-[3-(N,N-Dicarbomethoxymethyl) phenoxy]-4-oxo-4H-quinolizine-3-carboxylate (18)

A suspension of ethyl 8-(3-nitrophenoxy)-4-oxo-4H-quinolizine-3-carboxylate (16) (710 mg, 2 mmol), and Pd (200 mg, 5%) on carbon in 25 ml ethanol was stirred under ambient hydrogen pressure for 6 h. The resulting deep yellow solution was filtered from the catalyst, and the solvent was evaporated to give 650 mg of the crude amine as a golden brown crystalline solid. The amine was dissolved in 9 ml acetonitrile, followed by addition of NaI (1.5 g, 10 mmol), methyl bromoacetate (1 ml, 10 mmol), and PROTON SPONGE® (2.6 g, 12 mmol). The reaction mixture was refluxed for 16 h, cooled to room temperature and poured into 200 ml ethyl acetate. The organic layer was washed with 200 ml portions of buffer (pH 2) until an acid reaction was indicated on litmus paper. The solvent was evaporated and the crude product was purified by flash chromatography, to give a bright yellow powder (310 mg, 30% over two steps). M.p. 161–163° C. $^1$H NMR ($\delta$, CDCl$_3$): 1.41 (t, J=7 Hz, 3H), 3.76 (s, 6H), 4.16 (s, 4H), 4.39 (q, J=7 Hz, 2H), 6.29–6.45 (m, 2H) 651–6.64 (m, 2H), 6.71 (d, J=2 Hz, 1H), 6.97 (dd, J=2 Hz, J=7 Hz, 1H), 7.32 (dd, J=8 Hz, J=8 Hz, 1H), 8.26 (d, J=8 Hz, 1H), 9.38 (d, J=8 Hz, 1H). MS: m/z 468.1535; required for $C_{24}H_{24}N_2O_8$: 468.1532.

EXAMPLE 14

Preparation of Ethyl 8-(Dicarbomethyoxymethyl)-4-oxo-4H-quinolizine-3-carboxylate (19)

A solution of Na[CH(CO$_2$Me)] in DMSO was prepared by adding dimethylmalonate (5.6 g, 42 mmol) in 10 ml DMSO to a suspension of NaH (2.0 g of a 60% suspension in oil, 50 mmol, and washed with hexane) in 10 ml DMSO. An oven-dried, 250 ml three-necked round-bottom flask equipped with a 100 ml dropping funnel containing the freshly prepared malonate anion solution, was charged with ethyl 8-chloro-4-oxo-4H-quinolizine-3-carboxylate (2) (3.76 g, 15.3 mmol) and 20 ml DMSO. The malonate anion solution was added rapidly to the reaction mixture and stirring was continued overnight. The reaction mixture was poured into 500 ml water and extracted three times with 400 ml dichloromethane. The organic solvent was evaporated and the crude product stirred overnight with 20 ml ethyl acetate. Filtration and drying in vacuo gave a yellow powder (3.22 g, 63%). M.p. 195–197° C. $^1$H NMR ($\delta$, CDCl$_3$): 1.42 (t, J=7 Hz, 3H), 3.82 (s, 6H), 4.41 (q, J=7 Hz, 2H), 4.73 (s, 1H), 6.64 (d, J 8 Hz, 1H), 7.22 (d, J=8 Hz, 1H), 7.59 (s, 1H), 8.41 (d, J=8 Hz, 1H), 9.34 (d, J=7 Hz, 1H). MS: m/z 347.1021; required for $C_{17}H_{17}NO_7$: 347.1004.

EXAMPLE 15

Preparation of Ethyl 8-[1,1-Dicarbomethoxy-2-carboethoxy-ethyl]-4-oxo-4H-quinolizine-3-carboxylate (20)

An oven-dried 50 ml three-necked round-bottom flask equipped with a reflux condenser was charged with NaH (160 mg, 60% suspension in oil, 4 mmol, washed with hexane) and 10 ml THF. Ethyl 8-(dicarbomethoxymethyl)-4-oxo-4H-quinolizine-3-carboxylate (19) (700 mg, 2 mmol) was added in three portions and stirring was continued for 1 h, followed by addition of ethyl bromoacetate (0.5 ml, 5.3 mmol). The reaction mixture was refluxed overnight, cooled to room temperature and poured into 100 ml water. The aqueous layer was extracted three times with 100 ml dichloromethane. The organic solvent was evaporated and the crude product was purified by flash chromatography (ethyl acetate) to give a yellow viscous oil (630 mg, 74%). 1H NMR ($\delta$, CDCl$_3$): 1.24 (t, J=7 Hz, 3H), 1.42 (t, J=7 Hz, 3H), 3.39 (s, 2H), 3.84 (s, 6H), 4.14 (q, J=7 Hz, 2H), 4.41 (q, J=7 Hz, 2H), 6.63 (d, J=8 Hz, 1H), 7.14 (dd, J=2 Hz, J=7 Hz, 1H), 7.61 (d, J=2 Hz, 1H), 8.40 (d, J=8 Hz, 1H), 9.29 (d, J=8 Hz, 1H). MS: m/z 433.1363; required for $C_{21}H_{21}NO_9$: 433.1372.

EXAMPLE 16

Preparation of Ethyl 1-Bromo-8-(1,1-dicarbomethoxy-2-carboethoxyethyl)-4-oxo-4H-quinolizine-3-carboxylate (21)

Using the bromination procedure described in Example 7 (i.e., for compound 9), ethyl 1-bromo-8-(1,1-dicarbomethoxy-2-carboethoxyethyl)-4-oxo-4H-quinolizine-3-carboxylate was isolated as an orange mass in a yield of 75% by flash chromatography (ethyl acetate). $^1$H NMR ($\delta$, CDCl$_3$): 1.26 (t, J=7 Hz, 3H), 1.42 (t, J=7 Hz, 3H), 3.45 (s, 2H), 3.85 (s, 6H), 4.16 (q, J=7 Hz, 2H), 4.41 (q, J=7 Hz, 2H), 7.33 (d, J=8 Hz, 1H), 8.06 (s, 1H), 8.61 (s, 1H), 9.36 (d, J=8 Hz, 1H). MS: m/z 511.0473; required for $C_{21}H_{22}BrNO_9$: 511.0477.

EXAMPLE 17

Preparation of Ethyl 8-(4-Methoxyphenyl)-4-oxo-4H-quinolizine-3-carboxylate (22)

An oven-dried 50 ml round-bottom flask equipped with reflux condenser was purged with argon, followed by addition of ethyl 8-chloro-4-oxo-4H-quinolizine-3-carboxylate (2) (500 mg, 2 mmol), 4-methoxyphenylboronic acid (372 mg, 2.4 mmol), CsF (600 mg, 3.9 mmol), PdCl$_2$[P(c-Hex)$_3$]$_2$ (80 mg, 0.1 mmol) and 6 ml DMF. The reaction mixture was stirred at 110° C. for 12 h and cooled to room temperature. Completion of the reaction was indicated by thin layer chromatography (ethyl acetate). The reaction mixture was poured into 100 ml water and extracted three times with 100 ml chloroform. The combined organic layers were washed three times with 50 ml water. The organic solvent was evaporated and the crude product was further purified by column chromatography (5% MeOH in ethyl acetate) to give a bright yellow solid (340 mg, 50% yield). M.p. 205–209° C. $^1$H NMR (δ, CDCl$_3$): 1.43 (t, J=7 Hz, 3H), 3.90 (s, 3H), 4.42 (q, J=7 H, 2H), 6.65 (d, J=8 Hz, 1H), 7.05 (d, J=9 Hz, 2H), 7.43 (dd, J=2 Hz, J=7 Hz, 1H), 7.58–7.80 (m, 3H), 8.37 (d, J=8 Hz, 1H), 9.41 (d, J=7 Hz, 1H). MS: m/z 323.1159; required for C$_{19}$H$_{17}$NO$_4$: 323.1157.

EXAMPLE 18

Preparation of Ethyl 8-(Naphth-1-yl)-4-oxo-4H-quinolizine-3-carboxylate (23)

Using the procedure as described in Example 17 (i.e., for compound 22) ethyl 8-(napthy-1-yl)-4-oxo-4H-quinolizine-3-carboxylate (23) was isolated in 51% yield by flash chromatography (ethyl acetate). M.p. 245–247° C. $^1$H NMR (δ, CDCl$_3$): 1.48 (t, J=7 Hz, 3H), 4.48 (q, J=7 Hz, 2H), 6.73 (d, J=8 Hz, 1H), 7.40 (dd, J=2 Hz, J=8 Hz, 1H), 7.55–7.64 (m, 4H), 7.72 (s, 1H), 7.91 (d, J=8 Hz, 1H), 7.98–8.06 (m, 2H), 8.48 (d, J=8 Hz, 1H), 9.52 (d, J=8 Hz, 1H). MS: m/z 343.1213; required for C$_{22}$H$_{17}$NO$_3$: 343.1208.

EXAMPLE 19

Preparation of Ethyl 8-(Benzo[b]fur-2-yl)-4-oxo-4H-quinolizine-3-carboxylate (24)

Using the procedure as described in Example 17 (i.e., for compound 22), ethyl 8-(benzo[b]fur-2-yl)-4-oxo-4H-quinolizine-3-carboxylate (24) was isolated in 48% yield by flash chromatography (ethyl acetate). M.p. 195–197° C. $^1$H NMR (δ, CDCl$_3$): 1.43 (t, J=7 Hz, 3H), 4.42 (q, J=7 Hz, 2H), 6.72 (d, J=8 Hz, 1H), 7.22–7.54 (m, 4H), 7.57 (d, J=8 Hz, 1H), 7.67 (d, J=8 Hz, 1H), 7.96 (d, J=1 Hz, 1H), 8.40 (d, J=8 Hz, 1H), 9.37 (d, J=8 Hz, 1H). MS: m/z 333.1011; required for C$_{20}$H$_{15}$NO$_4$: 333.1000.

EXAMPLE 20

Preparation of 4-oxo-4H-Quinolizine-3-carboxylic Acid (1a)

To a suspension of ethyl 4-oxo-4H-quinolizine-3-carboxylate (1) (100 mg, 0.46 mmol) in 4 ml methanol was added 300 μl NaOH (3 M). The reaction mixture was stirred overnight, followed by evaporation of the solvent in vacuo. The remaining solid was dissolved in 4 ml water and the clear solution was acidified to pH 1, with 1 M HCl. The resulting suspension was filtered, and the residue was dried in vacuo over P$_2$O$_5$ to give yellow plates of 4-oxo-4H-quinolizine-3-carboxylic acid (1a) (63 mg, 72%). M.p. 235–240° C. $^1$H NMR (δ, DMSO-d$_6$): 7.26 (d, J=8 Hz, 1H), 7.64 (dd, J=7 Hz, J=7 Hz, 1H), 8.03 (dd, J=7 Hz, J=7 Hz, 1H), 8.14 (d, J=9 Hz, 1H), 8.39 (d, J=9 Hz, 1H), 9.27 (d, J=7 Hz), 14.13 (s, 1H). MS: m/z 189.0433; required for C$_{12}$H$_{11}$NO$_3$: 189.0428.

EXAMPLE 21

Preparation of 4-oxo-8-Chloro-4H-quinolizine-3-carboxylic Acid (2a)

Using the procedure as described in Example 20 (i.e., for 1a), 4-oxo-8-chloro-4H-quinolizine-3-carboxylic acid (2a) was isolated in 52% yield. M.p.>250° C. $^1$H NMR (δ, DMSO-d$_6$): 7.13 (d, J=9 Hz, 1H), 7.62 (d, J=7 Hz, 1H), 8.34 (s, 1H), 8.40 (d, J=8 Hz, 1H), 9.16 (d, J=7 Hz, 1H). MS: m/z 223.0028; required for C$_{10}$H$_6$NO$_3$: 223.0036.

EXAMPLE 22

Preparation of [6,7]Benzo-4-oxo-4H-quinolizine-3-carboxylic Acid (3a)

Using the procedure as described in Example 20 (i.e., for compound 1a), [6,7]benzo-4-oxo-4H-quinolizine-3-carboxylic acid (3a) was obtained as a red powder in 50% yield. M.p.>250° C. $^1$H NMR (δ, CDCl$_3$): 6.90 (d, J=8 Hz, 1H), 7.33 (d, J=9 Hz, 1H), 7.60–7.83 (m, 4H), 8.68 (d, J=8 Hz, 1H), 9.96 (d, J=9 Hz, 1H), 14.38 (s, 1H). MS: m/z 239.0575; required for C$_{14}$H$_9$NO$_3$: 239.0592.

EXAMPLE 23

Preparation of 1-Bromo-4-oxo-4H-quinolizine-3-carboxylic Acid (9a)

Using the procedure as described in Example 20 (i.e., for compound 1a), 1-bromo-4-oxo-4H-quinolizine-3-carboxylic acid (9a) was obtained as a bright yellow powder in 57% yield. M.p.>250° C. $^1$H NMR (δ, DMSO-d$_6$): 7.76 (dd, J=7 Hz, J=7 Hz, 1H), 8.20–8.32 (m, 2H), 8.53 (s, 1H), 9.41 (d, J=7 Hz, 1H). MS: m/z 273.9693; required for C$_{10}$H$_6$BrNO$_3$—Li: 273.9691.

EXAMPLE 24

Preparation of 1-N,N-di(Carboxymethyl)]-4-oxo-4H-quinolizine-3-carboxylic Acid (11a)

Using the procedure as described in Example 20 (i.e., for compound 1a), 1-[N,N-di(carboxymethyl)]-4-oxo-4H-quinolizine-3-carboxylic acid (11a) was obtained as a bright yellow powder in 50% yield. M.p. 231–234° C. $^1$H NMR (δ, D$_2$O): 3.80 (s, 4H), 7.66 (dd, J=7 Hz, J=7 Hz, 1H), 8.07 (dd, J=7 Hz, J=7 Hz, 1H), 8.32 (s, 1H), 8.63 (d, J=8 Hz, 1H), 9.33 (d, J=7 Hz, 1H). MS: m/z 276.0745 (M-CO$_2$); required for C$_{13}$H$_{12}$N$_2$O$_5$: 276.0746.

EXAMPLE 25

Preparation of 1-(2,2-Dicarboxyvinyl)-4-oxo-4H-quinolizine-3-carboxylic Acid (12a)

Using the procedure as described in Example 20 (i.e., for compound 1a), 1-(2,2-dicarboxyvinyl)-4-oxo-4H-quinolizine-3-carboxylic acid (12a) was obtained as a bright yellow powder in 61% yield. M.p.>250° C. $^1$H NMR (δ, DMSO-d$_6$): 7.72 (dd, J=7 Hz, J=7 Hz, 1H), 7.90 (s, 1H), 8.13 (dd, J=7 Hz, J=7 Hz, 1H), 8.26 J=9 Hz, 1H), 8.57 (s, 1H), 9.36 (d, J=7 Hz). MS: m/z 215.0591 (M-CO$_2$); required for C$_{12}$H$_9$NO$_3$: 215.0582.

EXAMPLE 26

Preparation of 1-(2,2-Dicarboxyethyl)-4-oxo-4H-quinolizine-3-carboxylic Acid (13a)

Using the procedure as described in Example 20 (i.e., for compound 1a), 1-(2,2-dicarboxyethyl)-4-oxo-4H-quinolizine-3-carboxylic acid (13a) was obtained as a bright yellow powder in 49% yield. M.p.>250° C. $^1$H NMR (δ, D$_2$O, 1% NaOD): 3.32 (d, J=7 Hz, 2H), 3.42 (t, J=7 Hz, 1H), 7.37 (dd, J=7 Hz, J=7 Hz, (dd, J=7 Hz, J=7 Hz, 1H), 8.01 (s, 1H), 8.02 (d, J=7 Hz, 1H), 9.22 (d, J=7 Hz, 1H). MS: m/z 261.0627 (M-2 $CO_2$); required for $C_{13}H_{11}NO_5$: 261.0637.

EXAMPLE 27

Preparation of 8-Amino-4-oxo-4H-quinolizine-3-carboxylic Acid (15a)

Using the procedure as described in Example 20 (i.e., for compound 1a), 8-amino-4-oxo-4H-quinolizine-3-carboxylic acid (15a) was obtained as a bright yellow powder in 61% yield. M.p.>250° C. $^1$H NMR ($\delta$, DMSO-$d_6$): 6.61 (d, J=9 Hz, 1H), 6.71 (d, J=2 Hz, 1H), 6.96 (dd, J=2 Hz, J=8 Hz, 1H), 7.6 (br), 7.82 (d, J=9 Hz, 1H), 8.95 (J=7 Hz, 1H). MS: m/z 160.0634 (M-$CO_2$; required for $C_9H_8N_2O$: 160.06366.

EXAMPLE 28

Preparation of 8-[3-(N,N-di(Carboxymethyl)phenoxy]-4-oxo-4H-quinolizine-3-carboxylic Acid (18a)

Using the procedure as described in Example 20 (i.e., for compound 1a), 8-[3-(N,N-di(carboxymethyl)phenoxy]-4-oxo-4H-quinolizine-3-carboxylic acid (18a) was obtained as a bright yellow powder in 71% yield. M.p. 231–234° C. $^1$H NMR ($\delta$, $D_2O$): 3.98 (s, 4H), 6.38 (s, 1H), 6.52 (d, J=7 Hz, 1H), 6.57 (d, J=8 Hz, 1H), 6.75 (d, J=9 Hz, 1H), 7.08 (s, 1H), 7.23–7.47 (m, 2H), 8.06 (d, J=8 Hz, 1H), 9.12 (d, J=8 Hz, 1H). MS: m/z 350.0160 (M-$CO_2$-$H_2O$); required for $C_{19}H_{14}N_2O_5$: 350.2359.

EXAMPLE 29

Preparation of 8-(Carboxymethyl)-4-oxo-4H-quinolizine-3-carboxylic Acid (19a)

Using the procedure as described in Example 20 (i.e., for compound 1a), 8-(carboxymethyl)-4-oxo-4H-quinolizine-3-carboxylic acid (19a) was obtained as a yellow powder in 68% yield. M.p.>250° C. $^1$H NMR ($\delta$, $D_2O$): 3.77 (s, 2H), 7.07 (d, J=8 Hz, 1H), 7.50 (d, J=7 Hz, 1H), 7.78 (s, 1H), 8.26 (d, J=8 Hz, 1H), 9.13 (d, J=7 Hz). MS: m/z 203.0575 (M-$CO_2$); required for $C_{11}H_{19}NO_3$: 203.0582.

EXAMPLE 30

Preparation of 8-(1,2-Dicarboxyethyl)-4-oxo-4H-quinolizine-3-carboxylic Acid (20a)

Saponification of (20) was done as described for (1). After completion of the reaction, the solvent was evaporated in vacuo, and the resulting yellow solid was dissolved in water. The aqueous layer was acidified to pH 1, and extracted three times with ethyl acetate. Evaporation of the organic solvent gave 8-(1,2-dicarboxyethyl)-4-oxo-4H-quinolizine-3-carboxylic acid (20a) as a yellow solid in 48% yield. M.p. 250° C. $^1$H NMR ($\delta$, DMSO-$d_6$): 2.72–2.76 (m, 2H), 3.02–3.06 (m, 1H), 7.14 (d, J=9 Hz, 1H), 7.60 (dd, J=2 Hz, J=9 Hz, 1H), 7.99 (s, 1H), 8.34 (d, J=9 Hz, 1H), 9.20 (d, J=9 Hz, 1H). MS: m/z 261.0601 (M-$CO_2$); required for $C_{13}H_{11}NO_5$: 261.0637.

EXAMPLE 31

Preparation of 1-Bromo-8-(1,2-carboxyethyl)-4-oxo-4H-quinolizine-3-carboxylic Acid (21a)

Using the procedure as described in Example 20 (i.e., for compound 1a), and heating the reaction mixture to 60° C., 1-bromo-8-(1,2-carboxyethyl)-4-oxo-4H-quinolizine-3-carboxylic acid (21a) was obtained as a yellow powder in 42% yield. M.p.>250° C. $^1$H NMR ($\delta$, $D_2O$, 1% NaOD): 2.74 (m, 1H), 2.94 (m, 1H), 4.05 (m, 1H), 7.35 (d, J=7 Hz, 1H), 8.01 (s, 1H), 8.33 (s, 1H), 9.17 (d, J=7 Hz, 1H). MS: m/z 389.9819; required for $C_{14}H_{10}BrNO_7Li$: 389.9801.

EXAMPLE 32

Preparation of 8-(4-Methoxyphenyl)-4-oxo-4H-quinolizine-3-carboxylic Acid (22a)

Using the procedure as described in Example 20 for (1a), 8-(4-methoxyphenyl)-4-oxo-4H-quinolizine-3-carboxylic acid (22a) was obtained as a yellow powder in 49% yield. M.p.>250° C. $^1$H NMR ($\delta$, $D_2O$): 3.62 (s, 3H), 6.40–6.62 (m, 3H), 7.11 (d, J=8 Hz, 1H), 7.16–7.32 (m, 3H), 7.94 (d, J=8 Hz, 1H), 8.64 (d, J=8 Hz, 1H). MS: m/z 278.0826 (M-OH); required for $C_{17}H_{12}NO_3$: 278.0817.

EXAMPLE 33

Preparation of 8-(Napth-1-yl)-4-oxo-4H-quinolinizine-3-carboxylic Acid (23a)

Using the procedure described for (1a) in Example 20, compound (23a) was obtained as a yellow powder in 67% yield, M.p. 245–247° C. $^1$H NMR ($\delta$, DMSO-$d_6$): 7.33 (d, J=8 Hz, 1H), 7.55–7.74 (m, 4H), 7.81 (dd, J=2 Hz, J=7 Hz, 1H), 8.04–8.17 (m, 2H), 8.35 (s, 1H), 8.45 (d, J=8 Hz, 1H), 9.36 (d, J=7 Hz, 1H). MS: m/z 315.0905; required for $C_{20}H_{13}NO_3$: 315.0895.

EXAMPLE 34

Preparation of 8-Benzo[b]furyl-4-oxo-4H-quinolizine-3-carboxylic Acid (24a)

Using the procedure as described in Example 20 for (1a), 8-benzo[b]furyl-4-oxo-4H-quinolizine-3-carboxylic acid (24a) was obtained as a yellow powder in 47% yield. M.p.>250° C. $^1$H NMR ($\delta$, DMSO-$d_6$): 7.26–7.40 (m, 2H), 7.48 (dd, J=8 Hz, J=8 Hz, 1H), 7.70 (d, J=8 Hz, 1H), 7.79 (d, J=8 Hz, 1H), 8.02 (s, 1H), 8.05 (dd, J=2 Hz, J=7 Hz, 1H), 8.38 (d, J=8 Hz, 1H), 8.52 (s, 1H), 9.24 (d, J=8 Hz, 1H). MS: m/z 305.0674; required for $C_{18}H_{11}NO_4$: 305.0687.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art of synthetic chemistry and/or related fields are intended to be within the scope of the following claims.

We claim:

1. A fluorescent magnesium indicator composition comprising a substituted carboxy-quinolizine bound selectively to magnesium, wherein said binding has a dissociation constant between about 0.4 mM to about 5.0 mM.

2. The composition of claim 1, wherein said carboxy-quinolizine is a substituted 4-oxo-4H-quinolizine-3-carboxylic acid.

3. The composition of claim 1, wherein said carboxy-quinolizine is substituted with a functional group at the C-1 position.

4. The composition of claim 3, wherein said functional group at said C-1 position is selected from the group consisting of bromide, $-N(CH_2CO_2Me)_2$, $-CH_2CH(CO_2Et)_2$, and $-CH=C-(CO_2Et)_2$.

5. The composition of claim 1, wherein said carboxy-quinolizine is substituted with a functional group at the C-1 and C-8 positions.

6. The composition of claim 3, wherein said functional group at said C-1 position is bromide.

7. A composition suitable for selective fluorescence detection of magnesium, comprising at least one substituted carboxy-quinolizine, wherein said carboxy-quinolizine is substituted with a functional group at the C-1 and C-8 positions and said functional group at said C-8 position is selected from the group consisting of $-C(CO_2Me_2)(CO_2Et)$, $-CH_2CO_2H$ and $-CH(CH_2CO_2H)(CO_2H)$.

8. A composition suitable for selective fluorescence detection of magnesium, comprising at least one substituted carboxy-quinolizine, wherein said carboxy-quinolizine is substituted with a functional group at the C-1 and C-8 positions and said functional group at said C-1 position is bromide, and said functional group at said C-8 position is $-C(CO_2Me_2)(CO_2Et)$.

9. The composition of claim 1, wherein said carboxy-quinolizine comprises at least two carboxyl groups.

10. The composition of claim 1, wherein said carboxy-quinolizine comprises a triacid.

11. The composition of cl wherein said carboxy-quinolizine has a dissociation constant of about 1 mM.

12. The composition of claim 1, wherein said substituted carboxy-quinolizine is selected from the group consisting of 4-oxo-8-chloro-4H-quinolizine-3-carboxylic acid, 4-oxo-8-chloro-4H-quinolizine-3-carboxylic acid, [6,7]-benzo-4-oxo-4H-quinolizine-3-carboxylic acid, 1-bromo-4-oxo-4H-quinolizine-3-carboxylic acid, 1-[N,N-di(carboxymethyl)]-4-oxo-4H-quinolizine-3-carboxylic acid, 1-(2,2-dicarboxyvinyl)-4-oxo-4H-quinolizine-3-carboxylic acid, 1-(2,2-dicarboxyethyl)-4-oxo-4H-quinolizine-3-carboxylic acid, 8-amino-4-oxo-4H-quinolizine-3-carboxylic acid, 8-[3-N,N-di(carboxymethyl)phenoxy]-4-oxo-4H-quinolizine-3-carboxylic acid, 8-carboxymethyl-4-oxo-4H-quinolizine-3-carboxylic acid, 8-(1,2-dicarboxyethyl)-4-oxo4H-quinolizine-3-carboxylic acid, 8-(4-methoxyphenyl)-4-oxo-4H-quinolizine-3-carboxylic acid, 8-(naphtha-1yl)-4-oxo-4H-quinolizine-3-carboxylic acid, and 8-(benzo[b]furyl)-4-oxo-4H-quinolizine-3-carboxylic acid.

13. A diagnostic reagent suitable for use for monitoring of physiological magnesium levels, said diagnostic reagent comprising a substituted carboxy-quinolizine bound selectively to magnesium, wherein said binding has a dissociation constant between about 0.4 mM to about 5.0 mM, and fluoresces upon binding to said magnesium.

14. The diagnostic reagent of claim 13 for monitoring of the magnesium levels of a patient suffering from or suspected of suffering from cardiovascular disease or hypertension.

* * * * *